(12) United States Patent
Strader et al.

(10) Patent No.: US 10,548,974 B2
(45) Date of Patent: Feb. 4, 2020

(54) THERAPEUTIC TREATMENT KIT FOR ALLERGIES BASED ON DNA PROFILES

(71) Applicant: ROCA MEDICAL LTD., London (GB)

(72) Inventors: James Strader, Austin, TX (US); Jovan Hutton Pulitzer, Frisco, TX (US)

(73) Assignee: ROCA Medical Ltd., London (GB)

( * ) Notice: Subject to any disclaimer, the term of this patent is extended or adjusted under 35 U.S.C. 154(b) by 516 days.

(21) Appl. No.: 15/222,790

(22) Filed: Jul. 28, 2016

(65) Prior Publication Data

US 2016/0367437 A1    Dec. 22, 2016

Related U.S. Application Data

(63) Continuation-in-part of application No. 15/183,719, filed on Jun. 15, 2016, now Pat. No. 10,369,215, which is a continuation-in-part of application No. 15/171,920, filed on Jun. 2, 2016.

(60) Provisional application No. 62/349,626, filed on Jun. 13, 2016, provisional application No. 62/198,067, filed on Jul. 28, 2015, provisional application No. 62/198,069, filed on Jul. 28, 2015, provisional application No. 62/198,071, filed on Jul. 28, 2015, (Continued)

(51) Int. Cl.
*A61K 39/35*    (2006.01)
*A61K 39/00*    (2006.01)

(52) U.S. Cl.
CPC ........ *A61K 39/35* (2013.01); *A61K 2039/545* (2013.01)

(58) Field of Classification Search
CPC .. A61K 39/35; A61K 2039/545; A61B 50/00; A61B 50/30; A61F 17/00; A61J 1/05; A61M 5/002
USPC .......................................... 206/570, 571, 572
See application file for complete search history.

(56) References Cited

U.S. PATENT DOCUMENTS 6,488,937 B1    12/2002   Smits
2003/0082212 A1    5/2003   Smits
(Continued)

OTHER PUBLICATIONS

PCT: European Patent Office Searching Authority, International Search Report and Written Opinion of PCT/IB2015/001330 (related application), dated Oct. 5, 2015, 14 pgs. dated Oct. 5, 2015.

(Continued)

*Primary Examiner* — Jacob K Ackun
*Assistant Examiner* — Jenine Pagan
(74) *Attorney, Agent, or Firm* — Gregory M. Howison

(57) ABSTRACT

A therapeutic treatment kit includes a container for holding a plurality of compartmentalized therapeutic dispensers. Each of the therapeutic dispensers includes a plurality of vials of antigens, and a plurality of containers of supplements disposed in compartments, each of the compartments labeled with the name of the supplement. A compartment is also provided for containing applicators or the antigens, such that an individual can extract the antigen from the vial in a single dose; and para instructions associated with a therapeutic program for utilizing the vials of antigens and the supplements in accordance with a therapeutic program that is predefined. The construction of the kit, including the dosages of the antigen, the types of antigens and the supplements all associated with a particular therapeutic program.

8 Claims, 19 Drawing Sheets

Related U.S. Application Data provisional application No. 62/176,000, filed on Jun. 15, 2015, provisional application No. 62/180,003, filed on Jun. 15, 2015, provisional application No. 62/169,787, filed on Jun. 2, 2015, provisional application No. 62/169,785, filed on Jun. 2, 2015.

(56) References Cited

U.S. PATENT DOCUMENTS

| | | | |
|---|---|---|---|
| 2006/0020514 A1 | 1/2006 | Yered | |
| 2006/0212318 A1 | 9/2006 | Dooley et al. | |
| 2009/0169602 A1 | 7/2009 | Senti et al. | |
| 2011/0233079 A1* | 9/2011 | Macinnes | A61M 25/002 206/232 |
| 2011/0236416 A1* | 9/2011 | Audonnet | A61K 39/15 424/199.1 |
| 2012/0076825 A1* | 3/2012 | Webster | A61K 9/0056 424/275.1 |
| 2012/0185276 A1* | 7/2012 | Shah | A61M 15/009 705/3 |
| 2013/0313156 A1* | 11/2013 | Duncan | A61M 5/1452 206/570 |
| 2014/0346068 A1* | 11/2014 | Omura | B65D 25/06 206/363 |
| 2016/0030368 A1* | 2/2016 | Atkins, Jr. | A61K 31/167 514/537 |
| 2016/0136049 A1* | 5/2016 | Weinstein | A61J 1/16 206/570 |
| 2016/0199257 A1* | 7/2016 | Husnu | B65B 3/003 206/570 |

OTHER PUBLICATIONS

Baumann L.S. et al., "Lip Silicone Granulomatous Foreign Body Reaction Treaded with Aldara (Imiquimod 5%)", Dermatologic Surgery Apr. 1, 2003 US, vol. 29, No. 4, Apr. 1, 2003 (Apr. 1, 2003), pp. 429-432, XP002745005, ISSN: 1076-0512, p. 429, left-hand column, paragraph middle. Apr. 1, 2003.

Prieto-Garcia Alicia et al: "Autoimmune Progesterone Dematitis: Clinical Presentation and Management with Progesterone Desensitization for Successful In Vitro Fertilization", Fertility and Sterility, vol. 95, No. 3, Mar. 2011 (Mar. 2011), pp. 1121.e9-1121.e13, XP28147753, pp. 1121.e9, left-hand column p. 1121.e12, left-hand column, paragraph top Mar. 1, 2001.

Cox et al., J. Allergy Clin. Immunol. 2011; 127(1 ):S1-S55 Jan. 1, 2011.

El Maghraby et al. Eur. J. Pharma. Sci. 2008; 34:203-222 Apr. 18, 2008.

PCT: European Patent Office Searching Authority, International Search Report and Written Opinion of PCT/IB2016/001332 (related application), dated Nov. 24, 2016, 13 pgs. dated Nov. 24, 2016.

E. Alvarez-Cuesta et al., "Subcutaneous immunotherapy", Allergy, vol. 61, No. s82, Oct. 2006 (Oct. 2006), pp. 5-13, XP055319495, UK Oct. 1, 2006.

\* cited by examiner

| SINGLE ANTIGEN TABLE | | | | | | | | |
|---|---|---|---|---|---|---|---|---|
| NDC | ANTIGEN | DILUTION PROCEDURE | D1 (BASE) | D2 | D3 | D4 | D5 | D6 |
| XXX | CAT | STANDARD | X1 | X2 | X3 | X4 | X5 | X6 |
|  |  |  | Y1 | Y2 | Y3 | Y4 | Y5 | Y6 |
|  |  |  | Z1 | Z2 | Z3 | Z4 | Z5 | Z6 |
| ∘∘∘ | ∘∘ | ∘∘ | ∘∘∘ | ∘∘∘ | ∘∘∘ | ∘∘∘ | ∘∘∘ | ∘∘∘ |
| YYY | DOG | STANDARD | X1 | X2 | X3 | X4 | X5 | X6 |
|  |  |  | Y1 | Y2 | Y3 | Y4 | Y5 | Y6 |
|  |  |  | Z1 | Z2 | Z3 | Z4 | Z5 | Z6 |
| ∘∘∘ | ∘∘ | ∘∘ | ∘∘∘ | ∘∘∘ | ∘∘∘ | ∘∘∘ | ∘∘∘ | ∘∘∘ |

FIG. 12

| DILUTION PROCEDURE | D1 | D2 | D3 | D4 | D5 | D6 |
|---|---|---|---|---|---|---|
| S1 | Z1 | Z2 | Z3 | Z4 | Z5 | Z6 |
| S2 | Z1' | Z2' | Z3' | Z4' | Z5' | Z6' |
| S3 | Z1" | Z2" | Z3" | Z4" | Z5" | Z6" |

FIG. 12A

| NDC BASE | ANTIGEN | DILUTION PROCEDURE | D1 | D2 | D3 | D4 | D5 | D6 |
|---|---|---|---|---|---|---|---|---|
| XXX (1702) | $A_{n-2}$ | STANDARD | $X_1$ | $X_1$ | $X_1$ | $X_1$ | $X_1$ | $X_1$ |
| | $A_{n-1}$ | | $X_1$ | $X_1$ | $X_1$ | $X_1$ | $X_1$ | $X_1$ |
| | $A_n$ | | $X_1$ | $X_1$ | $X_1$ | $X_1$ | $X_1$ | $X_1$ |
| ⁰⁰⁰ | ⁰⁰⁰ | ⁰⁰⁰ | ⁰⁰⁰ | ⁰⁰⁰ | ⁰⁰⁰ | ⁰⁰⁰ | ⁰⁰⁰ | ⁰⁰⁰ |

THERAPEUTIC TREATMENT KIT FOR ALLERGIES BASED ON DNA PROFILES

CROSS-REFERENCE TO RELATED APPLICATIONS

This application is a Continuation-In-Part of U.S. application Ser. No. 15/183,719, filed on Jun. 15, 2016, entitled PREDILUTION SETS FOR DISTRIBUTING ANTIGENS. U.S. application Ser. No. 15/183,719 is a Continuation-In-Part of U.S. application Ser. No. 15/171,920, filed on Jun. 2, 2016, entitled METHOD FOR MANAGING REIMBURSEMENTS FOR PREVIOUSLY NON DATABASE ALLERGENS, which claims the benefit of U.S. Provisional Application No. 62/169,785, filed on Jun. 2, 2015, and entitled METHOD FOR MANAGING REIMBURSEMENTS FOR PREVIOUSLY NON DATABASE ALLERGENS, and of U.S. Provisional Application No. 62/169,787, filed on Jun. 2, 2015, entitled METHOD FOR REPURPOSING NDC CODES IN A PHARMACEUTICAL DATABASE FOR ALLERGENS. U.S. application Ser. No. 15/183,719 also claims the benefit of U.S. Provisional Application No. 62/180,003, filed on Jun. 15, 2015, entitled USE OF AUTOINJECTOR FOR DISTRIBUTING ANTIGENS TO THE PUBLIC, and of U.S. Provisional Application No. 62/176,000, filed on Jun. 15, 2015, entitled PREDILUTION SETS FOR DISTRIBUTING ANTIGENS. U.S. application Ser. No. 15/183,719 also claims the benefit of U.S. Provisional Application No. 62/349,626, filed on Jun. 13, 2016, entitled METHOD AND APPARATUS FOR COMPLETING PRESCRIPTION FOR ALLERGEN COCKTAIL WITH PATCH. This application also claims the benefit of U.S. Provisional Application No. 62/198,067, filed on Jul. 28, 2015, entitled SYSTEM FOR LINKING DNA PROFILE TO THERAPEUTIC TREATMENT OF ALLERGIES, and Provisional Application No. 62/198,069, filed on Jul. 28, 2015, entitled THERAPEUTIC TREATMENT KIT FOR ALLERGIES BASED ON DNA PROFILES. This application also claims the benefit of U.S. Provisional Application No. 62/198,071, filed on Jul. 28, 2016, entitled GENOME INDEX FOR THERAPEUTIC TREATMENT OF ALLERGY SUFFERERS. U.S. application Ser. Nos. 15/183,719, 15/171,920 and U.S. Provisional Application Nos. 62/169,785, 62/169,787, 62/180,003, 62/176,000, 62/349,626, 62/198,067, 62/198,069 and 62/198,071 are incorporated by reference herein in their entirety.

TECHNICAL FIELD

The following disclosure relates generally to the use of DNA profiles to therapeutic treatment with allergens.

BACKGROUND

Immunotherapy (IT) is recognized as one of the most curative treatment for allergies. By exposing the immune system to slowly increasing concentrations of immunomodulators such as an allergen or antigen, it will eventually stabilize and regain control the portion that is hypersensitive to the allergen or antigen. In general, immunotherapy is the "treatment of disease by inducing, enhancing, or suppressing an immune response." Immunotherapies designed to elicit or amplify an immune response are classified as activation immunotherapies, while immunotherapies that reduce or suppress are classified as suppression immunotherapies. The active agents of immunotherapy are collectively called immunomodulators. They are a diverse array of recombinant, synthetic and natural preparations, often cytokines.

Immunotherapy involved in the treatment of allergies is a type of suppression immunotherapy, often termed desensitization or hypo-sensitization. This is compared with allergy treatments such as antihistamines or corticosteroids which treat only the symptoms of allergic disease. Immunotherapy is the only available treatment that can modify the natural course of the allergies, by reducing sensitivity to the immunomodulators such as antigens or allergens. An antigen and an allergen can both cause one's immune system to respond. An allergen is an antigen, but not all antigens are allergens. An antigen is any substance that is capable of causing one's immune system to produce antibodies. They are typically organic, or living, produced proteins. An allergen is any antigen that causes an allergic reaction. A nonallergen antigen could be a bacteria, virus, parasite, or fungus that causes an infection. This could also be something else that causes antibody immune system response, like toxins, chemicals, tissue cells involved in transplants or blood cells from a blood transfusion. An allergen is an environmentally produced substance that causes an allergic reaction, although the substance may not be harmful. Allergens cause no reactions in some individuals, while possibly causing a hypersensitive reaction in others. Common allergens include such things as pollen, plants, smoke, feathers, perfumes, dust mites, toxic mold, food, drugs, animal dander, and insect bites and stings.

The exact mechanisms of how IT works are not fully understood, but they involve shifting a patient's immune response from a predominantly "allergic" T-lymphocyte response to a "non-allergic" T-lymphocyte response.

Current accepted processes for performing allergy immunotherapy include injecting immunomodulator matter in the form of antigen material into patient subjects. This is referred to as subcutaneous immunotherapy (SCIT), requiring a patient to visit a doctor's office for weekly injections. It's is very expensive and time-consuming. A second technique, sublingual immunotherapy (SLIT), involves the application of allergy extracts (antigens), and allergens placed into a pill form and swallowed by the patient or disposed in "allergy drops" which are placed under the tongue for the allergens/antigens to be absorbed into the oral mucosa. Transdermal patches may have been used without much success and mostly were used for patch testing to see if a patient reacts to various chemicals or allergens.

Of the people who start traditional subcutaneous injected immunotherapy (SCIT), 90% fail to complete their therapy due to needle fatigue and not being able to see a doctor in their office once or more per week for several years. Further, doctors charge for every one of those visits. Further, doctors trained to give injections for allergies are concentrated in high population and upper middle class places. People in rural areas and people who do not live in upper middle class areas cannot get to an allergist for shots. Consider an inner city kid having to ride public transportation and pay a high copay just to get a high risk injection if an alternative therapy were available!

Allergies are also linked to depression and suicide and are among the top ten reasons for missed work and lost productivity. Lastly, allergies and asthma result in billions of dollars in lost productivity and healthcare costs among the 90% of allergy patients that either never get immunotherapy or receive failed immunotherapy delivered under its current administration methods.

The determination of what type of allergies an individual is susceptible to can be determined based on a number of different techniques. The conventional technique is to use what is referred to as a "prick" test. This test involves disposing on a plurality of small needles the drop of allergen at a specified dose and "pricking" the skin of the individual with each of the needles in a predetermined pattern. Since the pattern map with the allergens, a later observation of the treated area on the skin of the individual will feel which allergens caused a symptomatic response, i.e., typically a swelling localized around the particular prick. By defining which of the pricks have a localized response, and the level of that response, a determination can be made as to what allergens a particular individual is susceptible to.

Another test that is being used more frequently is that associated with a blood test for allergens. Allergy blood tests detect and measure the amount of allergen-specific antibodies in the blood of an individual. When an individual comes into contact with an allergy trigger, known as an allergen, their body makes antibodies against it. These antibodies tell cells in their body to release certain chemicals and these chemicals are what cause allergy symptoms. The allergy blood tests usually screen for at least 10 common allergy triggers, including dust, pet dander, trees, grasses, weeds, and molds related to the locale in which an individual lives. These blood tests are also particularly helpful in diagnosing food allergies.

These allergy blood tests are sometimes referred to as immunoassay tests and include Enzyme-linked immunosorbent assay (ELISA, or EIA) and Radioallergosorbent test (RAST). The ELISA test measures the amount of allergen-specific antibodies in the individual's blood and the RAST test looks for specific allergen-related anti-bodies in order to identify an individual's allergy triggers. These blood tests can also check white blood cell counts, including a count of a type of white cell called the eosinophil.

Another area is that associated with Pharmacogenetics, which is basically an area involved with determining how one's genes respond to certain medications. This provides for determining the right drug for the right patient at the right dosage. This typically involves a DNA test. This DNA test allows the treating physician to prescribe medication that best suits a particular individual's DNA structure. The advancement of genetic research has led to far greater understanding of the importance of genetic disease and a demand for pharmacogenetics testing companies. Personalized medicine uses genetic information, lifestyle behavior, and other risk factors to tailor medical decisions and treatments to individual patients. Thus, a pharmacogenetics testing lab provides knowledge that helps physicians prescribing drug regimen the greater probability of a positive outcome. This is basically involved to some extent with predicting drug-drug interactions. Pharmacogenetics involves variation in genes involved in drug metabolism with a particular emphasis on improving drug safety. The use of pharmacogenetic testing provides the opportunity to improve prescribing safety and efficacy. For example, the drug Plavix blocks platelet reception and is the second best-selling prescription drug in the world; however, it is known to warrant different responses among patients. Certain studies have linked the gene CYP2C 19 to those who cannot normally metabolize Plavix. With knowledge of the presence of this gene, treatment regimen can prevent use of this drug.

SUMMARY

In one embodiment, a therapeutic treatment kit includes a container for holding a plurality of compartmentalized therapeutic dispensers is provided. The therapeutic treatment kit comprising each of the therapeutic dispensers including a plurality of vials of antigens, and a plurality of containers of supplements disposed in compartments, each of the compartments labeled with the name of the supplement. A compartment is also provided for containing applicators or the antigens, such that an individual can extract the antigen from the vial in a single dose; and para instructions associated with a therapeutic program for utilizing the vials of antigens and the supplements in accordance with a therapeutic program that is predefined. The construction of the kit, including the dosages of the antigen, the types of antigens and the supplements all associated with a particular therapeutic program.

BRIEF DESCRIPTION OF THE DRAWINGS

For a more complete understanding, reference is now made to the following description taken in conjunction with the accompanying Drawings in which:

FIG. 12 illustrates a diagrammatic view of a table in a relational database relating distributed doses back to NDC-bearing dose;

FIG. 12A illustrates a diagrammatic view of a table showing the dilution procedure;

DETAILED DESCRIPTION

Figure 1:
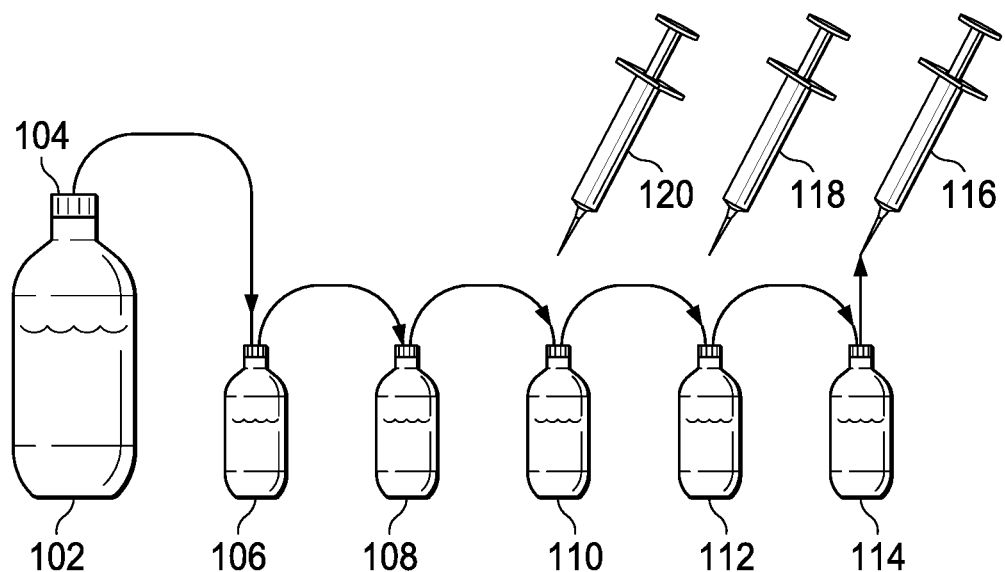
FIG. 1 illustrates a diagrammatic view of a dilution sequence of diluting a concentrated antigen extract.

Referring now to the drawings, wherein like reference numbers are used herein to designate like elements throughout, the various views and embodiments for a genome index for therapeutic treatment of allergy sufferers are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a depiction of a typical technique for diluting immunomodulators such as antigens, as one example. Preparation of a diluted antigen is performed first by receiving a bottle of extract concentrates from an approved vendor. These are formulated in a given weight/volume (w/v) format with a given antigen associated therewith. For typical antigens such as those associated with the cat antigen, these are relatively well controlled. Typically, a vendor will provide an extract for a single antigen or allergen. Allergens such as pollen and the such are not as well controlled due to the technique for collecting such. In any event, there are typically very few approved vendors for these extracts and allergist typically receives these vendor provided concentrates in a sufficient quantity to make the necessary diluted solution.

Allergen extract is typically comprised of a non-allergenic material, a non-allergenic protein and an allergenic protein. The extraction solutions can be aqueous containing saline and phenol which could be a glycerinated solution. The allergen is added, the units of measure are sometimes referred to as "AU" for "allergy units," typically used for mites. These are referred to as "AU/mL." For such things as grass and cats, the term "BAU" is used for "bioequivalent units." For other allergens, the terminology is, for example, 1:20 w/v, which stands for 1 g source material per 20 mL of fluid. The relationship between BAU and 1:20 w/v depends upon the extract. In any event, there is a defined amount of extract contained within the concentrate.

When concentrated extracts are formulated by an authorized vendor, they are typically provided in standardized versions and non-standardized versions. In standardized versions, they typically are provided in a 50% glycerin dilutant. They can either be a single allergen extract or they can be a mix. For example, one can obtain a "9 Southern Grass Mix (concentrate)" which contains equal parts of: 2 Bermuda at 10,000 BAU/mL, P27 7 Grass at 100,000 BAU/mL, and 15 Johnson at 1:20 w/v. For non-standardized extracts, these are typically provided in either a glycerin dilutant or an aqueous dilutant such as saline. They can be a single extract or a mix. Thus, whenever a concentrated extract is referred to hereinbelow, this refers to a formulation that is provided by an authorized vendor that can be diluted in accordance with the processes described hereinbelow. These are typically provided in the 50 mL bottles with a needle compatible top.

Referring back to FIG. 1, the extract concentrate is disposed in a bottle 102. This is a sterile concentrate that has an injection stoppered top 104. There are provided a plurality of five 5 mL sterile injection stoppered bottles 106, 108, 110, 112 and 114, although there could be more and the bottles or containers could be larger than 5 mL. Each of these bottles has disposed therein a defined amount of dilutant, depending upon what the final dilutant is required to be. Typically, the amount of dilutant is 4.5 mL. The procedure is to, first, extract a defined amount of the concentrated extract from the bottle 102 and dispose it in the bottle 106. This is facilitated by the sterile hypodermic that is inserted through the stopper at the top of the bottle 102 to extract concentrate and then the hypodermic is inserted through the stopper in the bottle 106 to inject extract from bottle 102 into bottle 106. Typically, the concentration in the concentrated extract bottle 102 is 1:20 w/v. This will result in a dilution of 1:10 in bottle 106. If the amount injected is 0.45 mL. Then, 0.45 mL of the diluted solution from bottle 106 is extracted and inserted into bottle 108, resulting in a 1:100 dilution of the original concentrate in model 108. The process is repeated up to the bottle 114 to provide a solution that is at a dilution of 1:100,000 of the original concentrate. This is a conventional way to provide a selected dilution of the original antigen. However, it should be understood that any concentration level can be provided from one bottle to the next. The purpose of using the sequential bottles is to allow an achievable portion of one bottle to be distributed to the next bottle, rather than trying to extract a very small amount of the initial concentrated extract. Typically, an allergist will then extract from the desired dilution an amount of the diluted antigen for injection percutaneously. Typically, desensitization is achieved by using the most diluted antigen level initially and sequentially moving up to a higher concentration level over time.

Illustrated in FIG. 1 are three hypodermic needles, one selecting a "dose" from bottle 114, and labeled hypodermic 116, a second hypodermic needle 118 for retrieving a dose from bottle 112, a third hypodermic needle 120 for extracting a dose from bottle 110. Each of the hypodermic needles 116, 118 and 120 will contain a different diluted dose. These would typically be separate needles in the event that the allergist or medical professional is injecting a patient. For other purposes, they could be the same needle, depending upon the dose or concentration required. A "dose" is defined by the amount of all the diluted product that would be required for the desired immunotherapy. This is defined by the medical professional. If, for example, bottle 112 were utilized, it may be that 1 mL of diluted solution constituted a "dose." It could be that less than 1 mL constituted a "dose."

In general, the typical distribution chain requires that the allergist or other medical professional purchase the base concentrate and then perform the dilution process. However, this procedure typically requires breaking the seal on the base concentrate bottle and then inserting a needle into the base concentrate bottle for the first dilution step. This occurs multiple times. Thus, multiple needles, each being sterile, can be used one time or, more commonly, a single needle is utilized in association with the base concentrate bottle, with the assumption that, since it does not involve insertion into human flesh, it is still sterile. In any event, this needle must penetrate the rubber stopper seal on the base concentrate bottles multiple times. In fact, these bottles could typically be held upside down and they would leak and, once the seal is broken, there is no sterile cover over the rubber stopper. This is a result of the multiple needle piercings of the rubber stopper. This is also the case with the small 5 mL bottles in that each has to be penetrated at least twice in the higher concentrate bottles. Thus, the last bottle that the allergist has would be a 5 mL bottle and this bottle would already have one piercing of the rubber stopper seal in order to provide the initial dilution level into the carrier material, such as saline. Thereafter, a patient might be able to receive 5 or 10 doses from that particular bottle, requiring 5 or 10 more piercings of the rubber stopper. During this time, of course, there is no seal over the rubber stopper.

Figure 2:
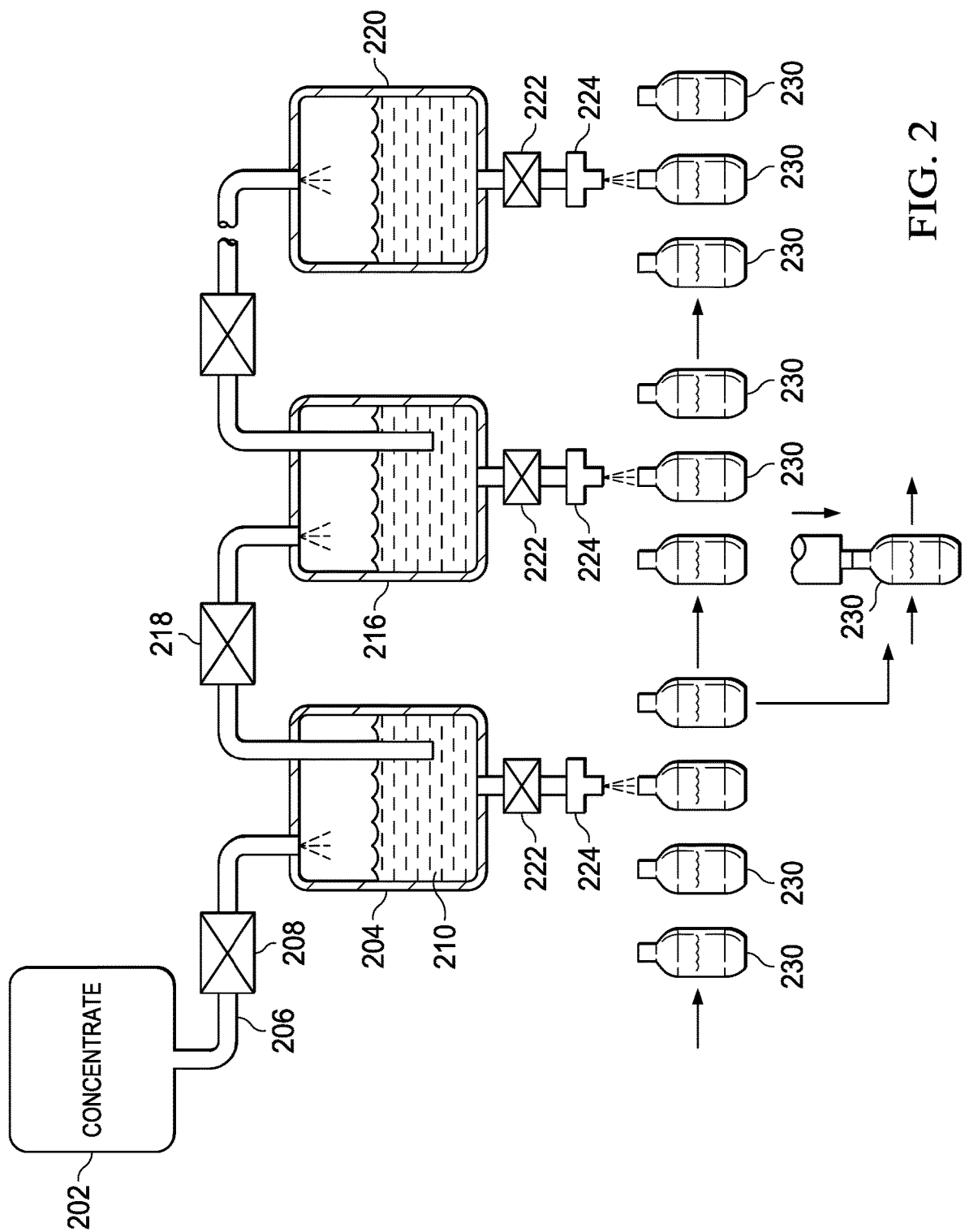
FIG. 2 illustrates a diagrammatic view of a production line for filling distribution bottles.
Figure 3:
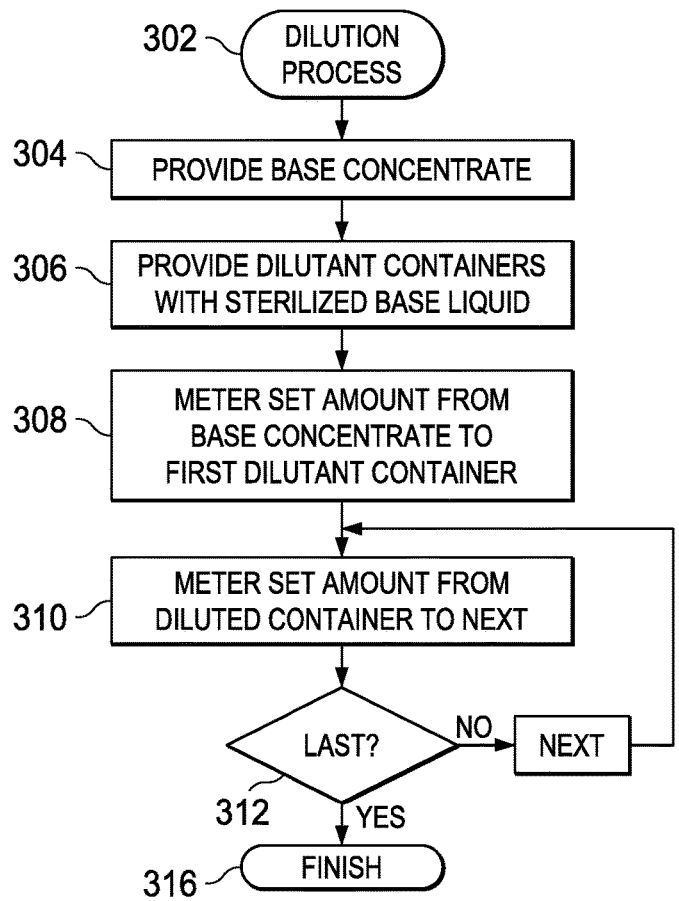
FIG. 3 illustrates a flow chart for the dilution process.
Figure 4:
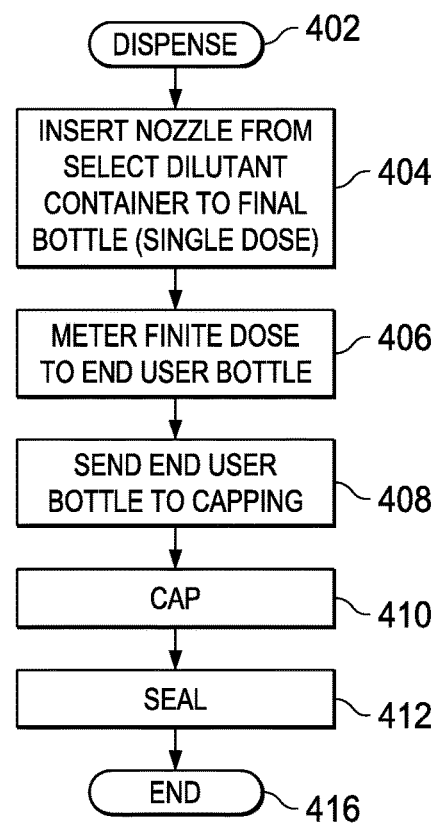
FIG. 4 illustrates a flow chart for the dispensing process.

In order to solve this problem, a process, in one embodiment, is provided whereby the concentrate bottles are produced from a sterile environment container which Artie has the dilutant provided thereto. This is illustrated in FIG. 2. In this embodiment, a large bottle of base concentrate 202 is provided at a first concentration. This is then metered into a first dilutant reservoir 204 via a tube 206 and a metering valve 208. The first dilutant container 204 has contained therein a carrier liquid 210 which can be, as described herein below, any of a number of materials, such as saline, glycol and the such. Typically, this depends upon the base carrier material associated with the concentrate 202. By knowing the volume of the material to 10 within the reservoir 204 prior to metering therein of the concentrate 202 with the metering valve 208, a very accurate amount of concentrate 202 can be dispensed within the reservoir 204. This metering valve 208 can be controlled to such a level that a very fine and controlled concentrated level can be defined. At this point in the process, the concentrate 202 defines a "batch" material that, for some allergens, is important. For example, if the allergen was related to pollen or the such, this can vary depending upon the year, the production harvest, the quality of harvest, etc. By defining a batch, and controlling the quality and the concentration level at each step in the dilution level, a very controlled dilution level can be provided for that particular batch.

Once the concentrated level or dilution level in the bottle has been defined, this is then utilized to provide a controlled amount of diluted allergen to a second dilution bottle 216 through a metering valve 218. This is repeated for multiple bottles down the line to a last bottle 220. Thus, there are then provided a plurality of larger vessels with controlled dilution levels at each diluted stage in a sterile environment. Each of these bottles 204, 216 and 220 has associated therewith a control metering valve 222 and a dispensing nozzle 224 that is operable to dispense diluted allergen material into a receptacle. This metering valve 222 and associated nozzle 224 are all approved to interface with an approved bottle.

In the dispensing process, there are provided for each dilution stage a plurality of bottles 230. Each of these bottles has a shape and opening that is approved to be interfaced with the nozzle. Each is passed by the nozzle and an exact amount of diluted material, the allergen, dispense therein. Thereafter, each bottle 230 is then subjected to a Procedure which inserts the rubber stopper and the seal there over. The result is a bottle with a defined dosage amount at a defined concentration level for a known batch of allergen, all of which is a sterile environment. The allergist or medical professional need only then remove this seal, insert the needle through the rubber stopper and extract the appropriate amount of diluted allergen. This particular bottle 230, in this embodiment, is designed to be a single dose. Thus, the actual amount of material disposed within the bottle will be approximately 1 mL. Typically, the bottles are 5 mL bottles. In this situation, that 5 mL bottle can be modified to maintain the same size but only provide for a single 1 mL dose. This will be described hereinbelow.

Referring now to FIG. 3, there is illustrated a flowchart for the overall dilution process, which is initiated at a block 302. The process flows to a block 304 to provide the base concentrate. As noted hereinabove, the base concentrate is typically associated with a fixed batch so that it is a well-controlled product and this is a sterile bottle within a sterile environment and the size can be larger than typically distributed to an allergist. The process flows to a block 306 wherein the various dilutant containers are provided with a sterilized base liquid such a saline or glycol, depending upon intended final use. The process then flows to block 308 wherein a metered amount of dilutant is passed from the base concentrate vessel to the first dilutant container. The process then flows to a block 310 wherein a metered amount of diluted allergen is transferred from the previous bottle to the next bottle until the last bottle is complete, which is determined at a decision block 312. This will then result in multiple vessels of diluted allergen at the appropriate diluted level for final dispensing. The program then flows to a block 316.

Referring now to FIG. 4, there is illustrated a flowchart for the dispensing operation, which is initiated at a block 402. The process flows to a block 404 wherein a nozzle is inserted from the select dilutant container or vessel to the final dispensing bottle, typically a single dose bottle. The process then flows to a block 406 to meter a finite dose to the end user bottle. Again, this could be a 1 mL dose in a 5 mL bottle or a 1 mL dose in a 1 mL bottle. The process then flows to a block 408 to send the end user bottle to capping, followed by a process block 410 to dispose a cap on the bottle, this being a rubber seal to allow insertion of the needle there through, and then to a seal block 412 to provide a sterile seal over the bottle and then to a terminate block 416.

Referring now to FIG. 5, there is illustrated in one embodiment a depiction of a delivery container for the final allergen in the bottles 230. The bottles would typically be controlled such that they would have, for example, a very distinctive color associated with each diluted level. The highest concentration bottle would be a bottle that would have to be carefully dispensed to a patient, as, if not adequately desensitized to the allergen, this could result in anaphylactic shock to the patient. Thus, it is important that the correct dose at the correct dilution level is administered at a particular time. This color coding process for any type of identification process clearly presents to the medical professional some clear indication of the concentrated level of allergen. Typically, these allergens will be provided in a kit form. For example, it may be that a patient would require the lowest concentrate level of the allergen three times per week for two weeks, followed by the next concentrated level of allergen two times per week for one week, etc. Thus, the various diluted levels of concentrate would be provided in single-dose bottles to, for example, a pharmacy, which would dispense the particular dosages. The first thing is that they would be from a common batch and they would be provided to the patient in the appropriate presentation. For example, the patient might receive a first box of six bottles 230 at the lowest concentrate level for the first two weeks. The pharmacist then would provide the second part of the prescription for the second level in the form of two bottles of concentrate at the next level, this all being color-coded. The box might be color-coded, as well as the bottles. Again, each of these bottles would be a single dose. Since they are all single-dose and contained within sterile bottles, the shelf life is considerably longer.

Referring now to FIG. 6, there is illustrated a cross-section of a typical bottle that would be involved with respect to the embodiment providing a single dose of 1 mL in a larger standard 5 mL bottle. A 5 mL bottle is represented by a bottle 602. This bottle 602 has an opening 604 that is provided for the 5 mL bottle. An insert 606 is provided for filling space within the bottle. This can be any type of plastic insert, etc. A smaller insert bottle 608 is disposed within the insert 606 to provide an elongated interior 620 which has a volume slightly in excess of 1 mL, such that a 1 mL dose can be disposed therein. This elongated interior is covered with a rubber stopper 622 such that a needle 624 can be disposed there through and be able to extract 1 mL of diluted antigen. If not for the elongated opening 620 facilitated by the insert 606 in the bottle 608, the 1 mL of diluted antigen would be disposed at a lower level and would be more difficult to extract.

Figure 7:
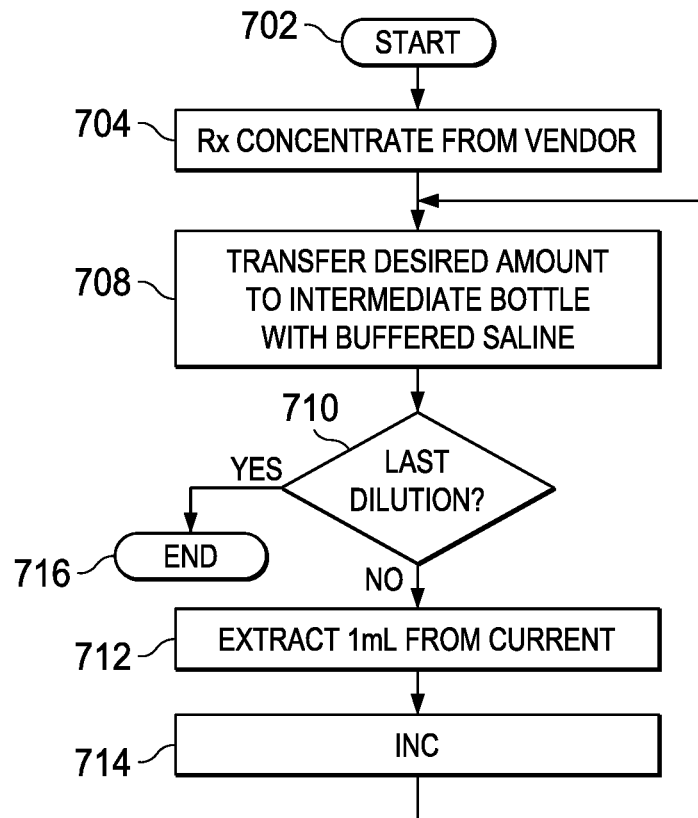
FIG. 7 illustrates a process flow for diluting an antigen extract.

Referring now to FIG. 7, there is illustrated a process flow for the embodiment of FIG. 1. This is initiated at a process block 702 and then proceeds to block 704 wherein a certain amount of concentrated extract is received from a vendor, this being a qualified or authorized vendor for the extract. This is typically at a predetermined concentrate level of, for example, 1:20 m/v. The process then flows to a block 708 wherein a defined quantity of, for example, 0.45 mL is transferred to a 5 mL bottle which already has a quantity of 4.5 mL buffered saline solution disposed therein. The process then flows to a block 710 to determine if this was the last dilution step needed, as described hereinabove, depending upon what level of dilution is necessary. If, for example, by steps of dilution are required for a particular patient, and all five steps would be processed. However, it is not necessary to do all five steps if an intermediate dilution is required. This essentially customizes the overall operation for a particular patient. Further, the industry is so regulated such that only 5 mL bottles can be utilized for this dilution process. Thus, it will only be a maximum of 5 mL of diluted material available at any step prior to proceeding to the next step. Thus, if all 5 mL are required, then the next step is not desired or useful. If it is not the last dilution step, the process flows to a block 712 to extract 0.45 mL of diluted antigen from the current 5 mL bottle and then flows back to the input of the process block 708 after incrementing the bottle count at a block 714. This continues until the last dilution, at which time the process flows from the block 710 to a terminate block 716. Again, any type of carrier could be utilized and bottles larger than 5 mL could in fact be utilized. This all depends upon the number of "doses" at a particular diluted level that are required by the physician right the initial script or prescription.

Figure 8:
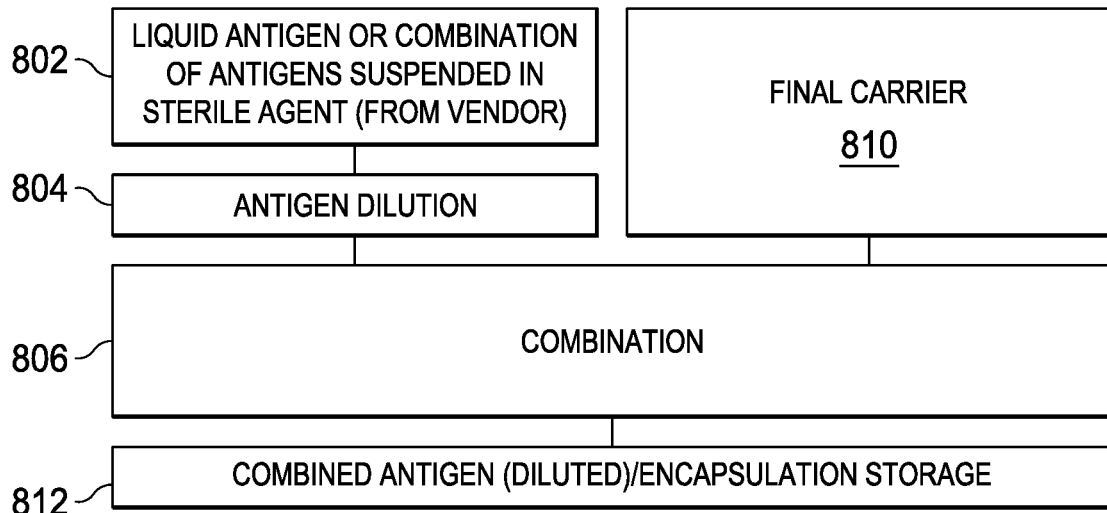
FIG. 8 illustrates a process flow for the overall distribution chain.

Referring now to FIG. 8, there is illustrated in overall flow of the operation of moving concentrated antigen from a vendor to an end user via a pharmacist. As noted hereinabove, the liquid antigen in a concentrated extract at the base concentrate level that has associated there with an NDC was first received from a vendor that assigned that NDC, which is basically a combination of a single antigen or antigens suspended in a sterile agent. This is indicated by a block 802. The antigen is then diluted by the pharmacist from this extract to a desired diluted level, as indicated by a process block 804. This is combined in a block 806 with a sterile carrier and containment material, i.e., sterile saline solution or, even a transdermal cream, for distribution to a patient. This, as described hereinabove, will typically be a defined number of doses of a single diluted antigen or multiple diluted antigens, wherein a dose is again defined as being a typical dose that a medical professional would administer to a patient in an office visit necessary to achieve a therapeutic result for which a patient could administer to themselves. This is either transferred as a combined antigen (diluted)/encapsulation product for storage on a shelf, as indicated by a block 812, or it would be transferred to a medical professional for a patient for management and disposition.

Figure 5:
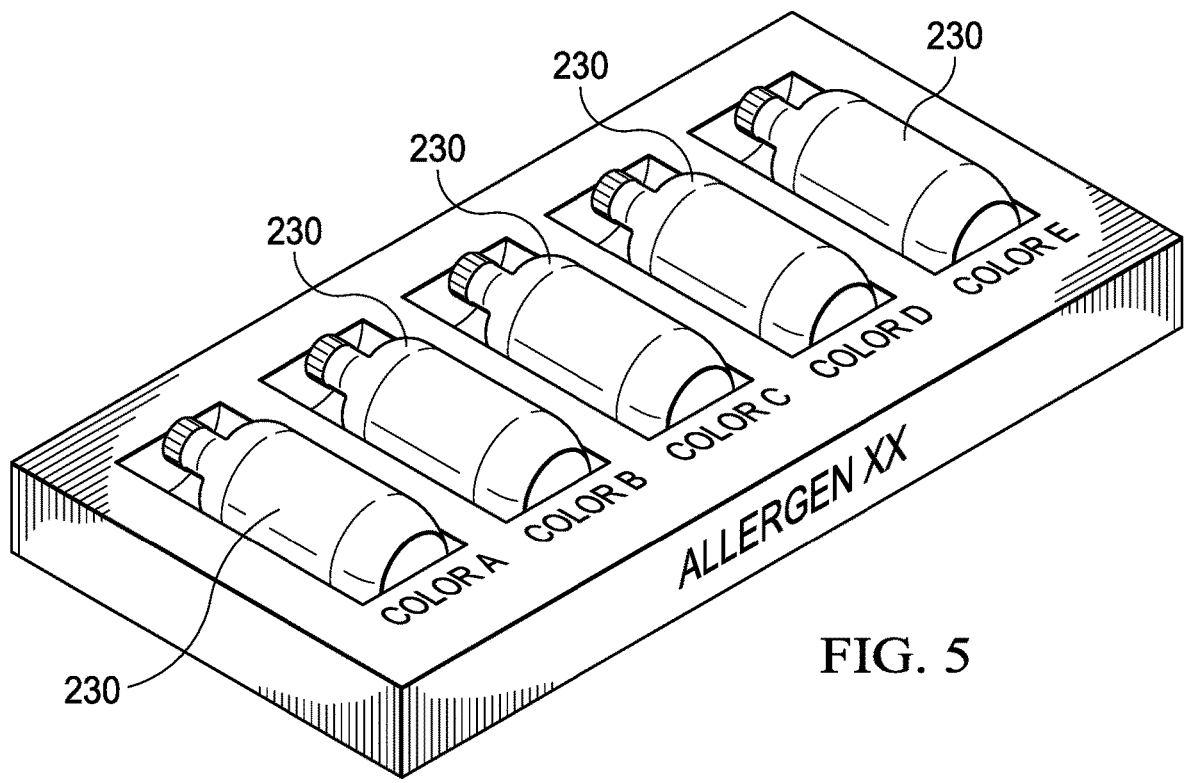
FIG. 5 illustrates a diagrammatic view of a color-coded box with different diluted levels of allergens.
Figure 6:
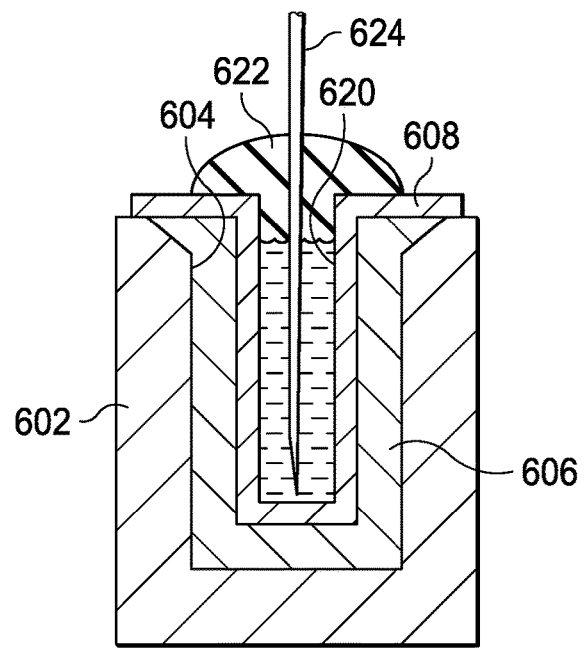
FIG. 6 illustrates a cross-sectional view of a low dose bottle.
Figure 9:
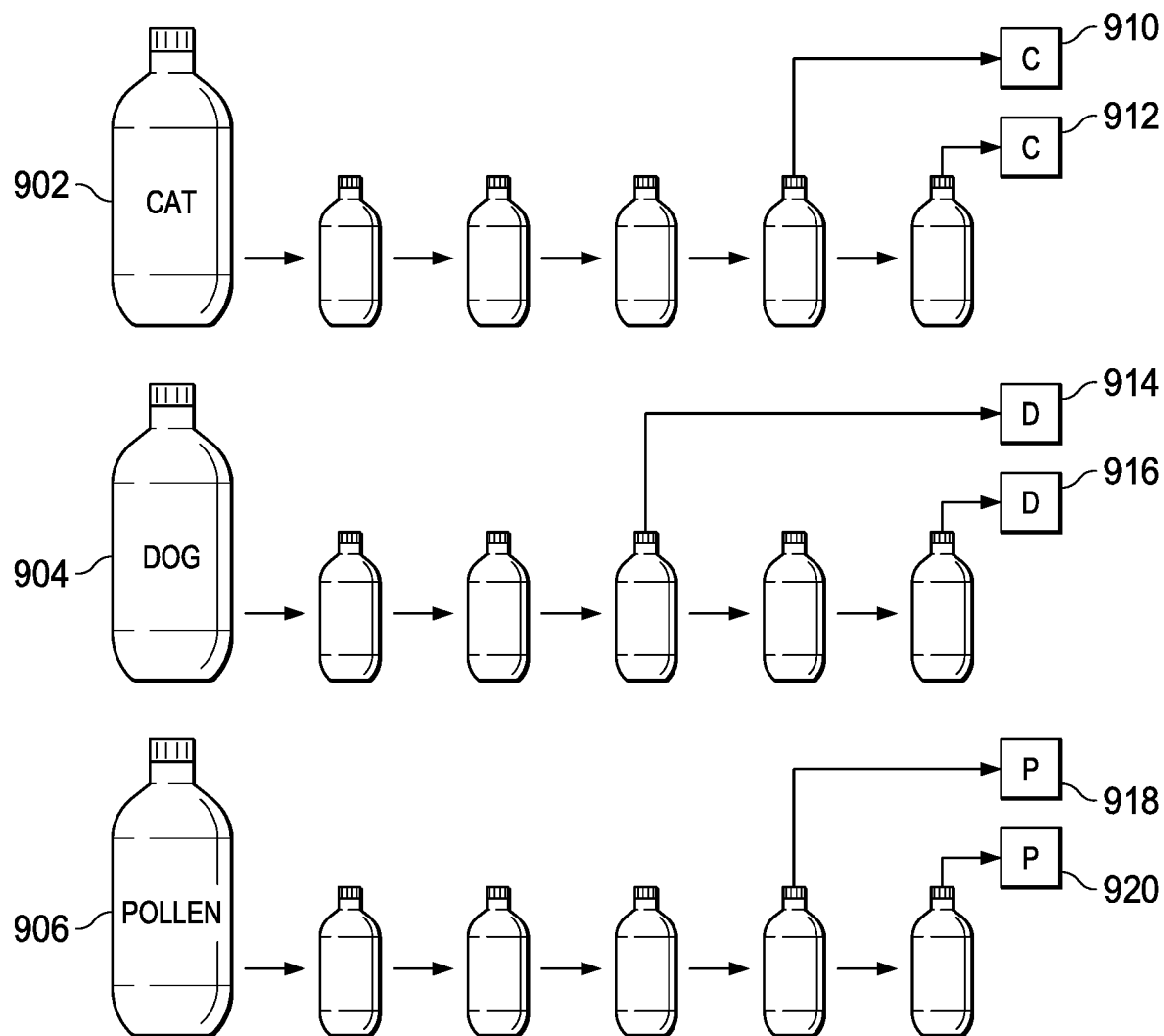
FIG. 9 illustrates a process flow for multiple extracts.

Referring now to FIG. 9, there is illustrated a diagrammatic view of three different extracts of antigens/allergens 902, 904 and 906. Each of these is for a particular antigen or allergen. The first two are for antigens respectively associated with a cat and a dog. The third is for an allergen associated with pollen. They are each diluted in accordance with the process described hereinabove with respect to FIG. 1. As illustrated, the antigen extract in bottle 902 is transferred as a diluted level to either an encapsulation material in a container 910 or 912, each at a different diluted level. This is similarly the case with respect to the antigen in bottle 904 and the allergen in 906 wherein the diluted level of the antigen in the bottle 904 is disposed in containers 914 and 916 and the diluted level of the allergen in bottle 906 is disposed in containers 918 and 920. Typically, any extract will be 100% pure with respect to the particular extract. These concentrated extracts are not typically mixed, which is typically a function that the medical professional or compounding pharmacist will perform. This, of course, is a customized mixture for a particular patient, i.e., this is a patient-specific combination as defined by the medical professional in the script provided to the pharmacist. For storage on the shelf, the operation of FIG. 9 will be facilitated in order to ensure that the containers 910-920 contained only a single antigen. Thus, when transferring the container to a store, for example, this would be stored on the shelf as a single allergen combination of the base concentrate level. The antigens/allergens 902, 904, and 906 may also have been part of the kit described with respect to FIG. 5. In that case, the pharmacist would still create a customized mix for the patient. For example, if the pharmacist received a kit for cat, dog, and pollen, and a prescription for a particular dosage of each (1 mL for example), the pharmacist would create a new bottle filled with one dose of antigen/allergen for cat, one dose for dog, and one dose for pollen. The dosage level (1 mL) may then be tracked back to the NDC code for each antigen/allergen. For example, if 1 mL of cat is associated with an NDC code having a price of $50 associated therewith, and the same is true for dog and pollen, then a total cost of $150 may be appropriate, allowing for the pharmacist to be reimbursed for that amount.

Figure 10:
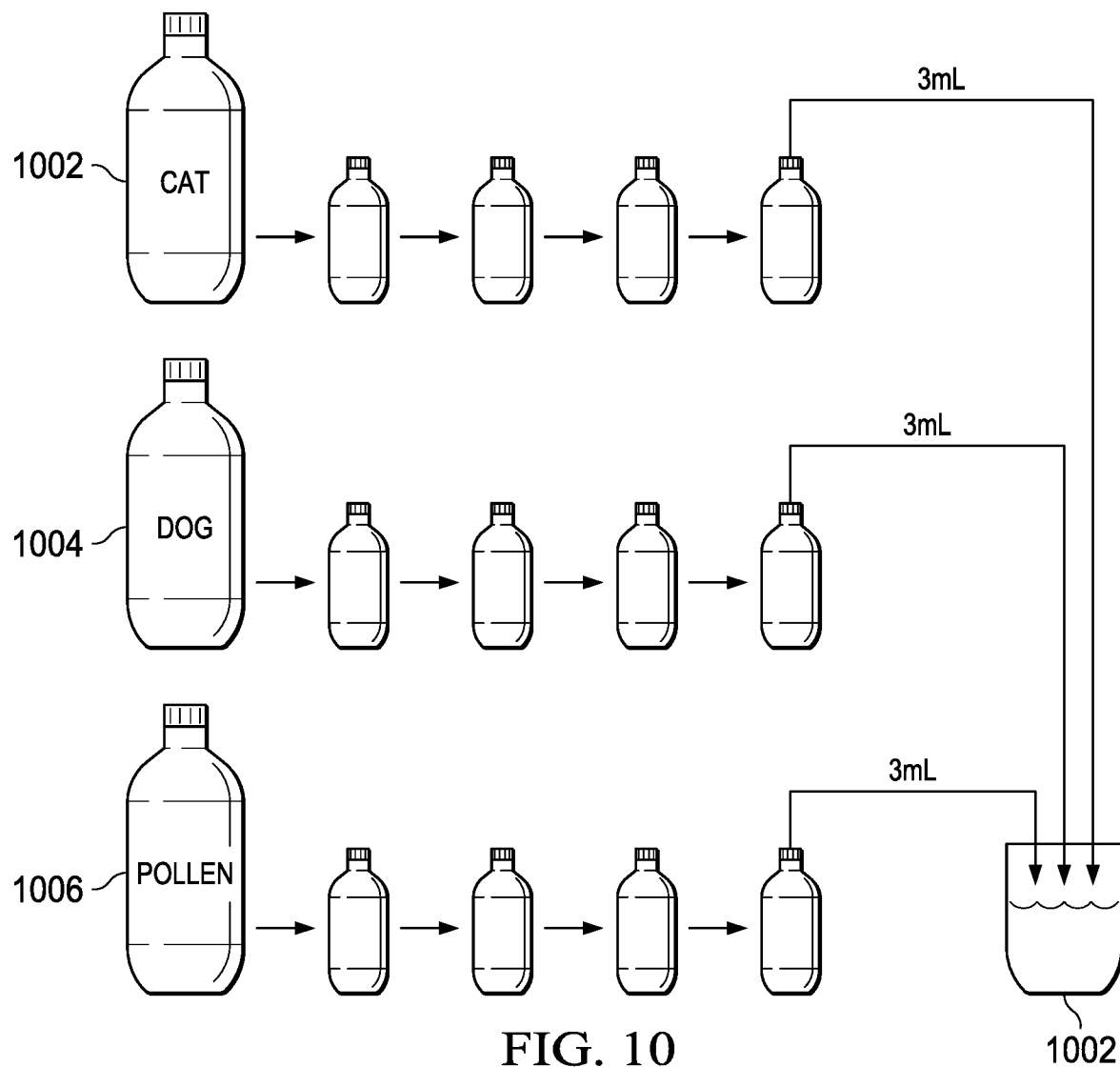
FIG. 10 illustrates an alternate embodiment of FIG. 9.

Referring now to FIG. 10, there is illustrated an alternate disclosure to that of the embodiment of FIG. 9. In this embodiment, each of the immunomodulators or antigens at the concentrated levels in the bottles 902-906 are diluted in accordance with the process noted hereinabove wherein they are sequentially diluted in the associated 5 mL bottles. However, note that only a maximum of 5 mL can be extracted from a given bottle at the last dilution level. If, in this example, it is desired to distribute a predefined number of doses to a final carrier 1002 having a fixed amount of carrier such as saline disposed therein and each dose will add to that material provide the final overall dosage or, alternatively, a viscous transdermal cream can be utilized that is initiated at an original fixed value in grants such that each dose will be associated with a single gram of that transdermal cream material, and then the amount of diluted antigen must be adjusted such that single dose is contained within 0.3 mL of the material. Thereafter, if 3 mL of antigen is extracted from a given bottle, this constitutes 30 doses such that a single dose will be associated with a single dose of the final encapsulation material. In this example, from each of the last dilution bottles for each of the concentrate bottles 902-904, 3 mL is extracted and inserted within the container 1002 containing prescribed level of carrier material, be that saline solution or a transdermal cream. Thus, for each milliliter of saline solution, for example, or each gram of transdermal cream material, there will be a single dose of the particular antigen associated there with. Thus, the carrier material in the container 1002 now acts as a consolidator of all of the antigens for a cocktail.

Figure 11:
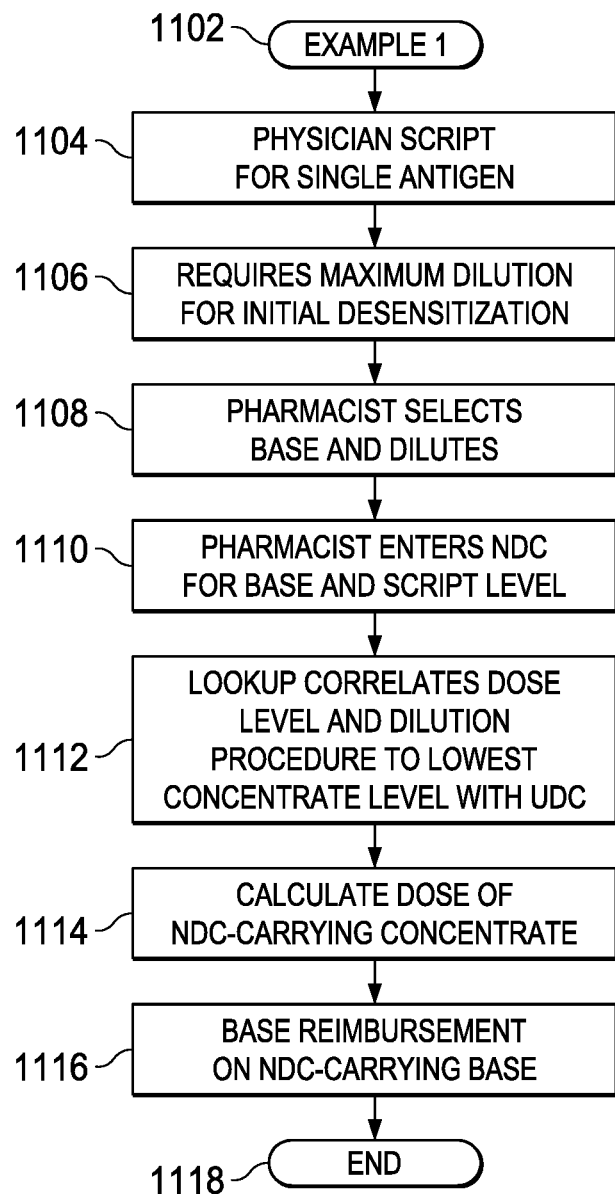
FIG. 11 illustrates a flowchart for one example of processing a physician script.

Referring now to FIG. 11, there is illustrated a flowchart depicting one example of the generation of a script for a single antigen and filling of that fiction based on that script and getting reimbursed therefor. This is initiated at a block 1102 and then proceeds to a block 1104 in order to prepare the physician script for a single antigen. The program then flows to a block 1106 in order to define the requirements of the maximum dilution for the initial desensitization. The physician defined at which level the script is written for. For example, the physician sets forth a regimen. This regimen defines six levels of dilution, each level of dilution are required for a predetermined amount of time. For example, the most diluted level might be required to be administered in three doses per week for three weeks for total of nine doses. The first script would require the pharmacist to deliver to the patient a file containing nine doses at that diluted level of the at least a single antigen. The physician could then require the second higher level to be provided over the course of one week at three doses per week. This might require a second script to be filled by the pharmacist or, alternatively, the pharmacist could fill that script that same time and maintained that particular vial on the shelf for distribution to the patient at a later time, all of this depending upon the script provided by the physician. Of course, the physician could require the patient to come into the office for observation and then write another script. This would be a separate and distinct operation and prescription which would be independently associated with a different set of benefits possibly.

After the dilution level is determined for the initial desensitization or at any level in the desensitization regimen, the program flows to a function block 1108 wherein the pharmacist selects concentrate antigen and then goes to the dilution process required order to achieve the desired diluted level. The program then proceeds to a function block 1110 where in the pharmacist enters the NDC code for the base concentrate level and the script level. Basically, what the pharmacist does is enter the antigen name and the dosage level provided by script. The program then proceeds to a function block 1112 in order to perform a lookup in the PBM database for the particular antigen that is associated with the script. This lookup does a correlation, as will be described hereinbelow, to the lowest concentrate level having an NDC for that particular antigen. Knowing the dilution level and the procedure, it is possible to determine what amount of the NDC-carrying concentrate level for that particular antigen was utilized and then a reimbursement obtained and four. This is indicated by the function block 1114 and 1116. The program then flows to an initial End block 1118.

Referring now to FIG. 12, there is illustrated a table for a single antigen and the overall crosscorrelation information. This is a relational database. In this table can be seen that there is provided a column for the NBC code which is populated for a particular antigen. This indicates the name of the antigen and also information associated there with. There is also a dilution procedure for multiple procedures that can be associated with administering this particular antigen. Since the NBC code associated only with the type of antigen but also the concentration levels, this will be associated with the dilution level to determine what the various dilutant levels are in the overall standard process. As noted, the base level is indicated by a dilutant level D1 or a base concentrate level there than provide five additional dilutant levels D2 through D6. Each one of these dilutant level columns has associated there with a particular range of dilutant levels. As indicated by example, there are levels 1 through 3 for each of diluted levels, with more possible. Therefore, if the most diluted level, D6 were selected and that the procedure required that the dilutant level Z6 for the dilutant level column D6 were selected as the N dilutant level that was required by the physician in the script provided to the pharmacist, this would be what was put into the PBM system. However, there is no NDC associated with this particular antigen at this particular dilutant level. Therefore there must be some crosscorrelation back to column D1 for the base concentrate level, which column has an NDC associated there with. If the final dilutant level was Z6, this could be cross correlated back within the same road to the dilutant level Z1 of the base concentrate. However, although not shown, there could actually be multiple roads associated with the dilutant level Z6, one for each dilution procedure. Thus, the crosscorrelation from the axle in dilutant level back to amount of bass constitute antigen required to process through the diluting procedure requires knowledge of the diluting procedure. This is illustrated in FIG. 12A, wherein each column for the dilutant level Z6 has three has such that there are provided three different amounts of the base extract that would be required, Z1, Z2' and Z". For example, it might be that this requires corresponding levels of 0.8 mL, 1.0 mL or 1.1 mL for those three different levels in order to accommodate the three different dilution procedures S1, S2 and S3. Thus, it is not just a mere crosscorrelation operation but, rather, and overall knowledge of the process that is required in order to determine how much actual product was utilized of the original base NDC-carrying antigen. Only when the amount of the base concentrate NDC-carrying antigen that is utilized is known can the actual dosage be determined. For reimbursement purposes, it is important to know whether 0.8 mL, 1.00 mL or 1.1 mL was use of the base concentrate NDC-carrying antigen is utilized. Reimbursement is calculated based upon this. However, all that is necessary for the pharmacist to do is to put in the end product that was generated and the procedure for coming up with that end product and relate that to the antigen that was utilized.

Figure 13:
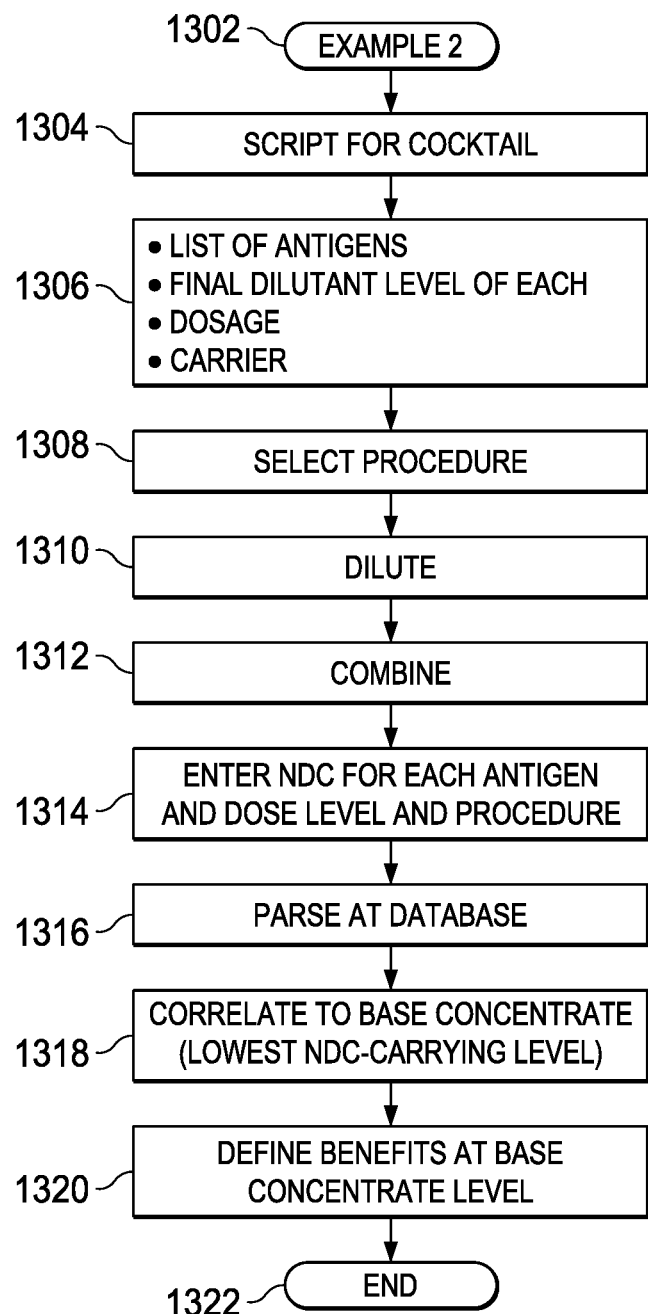
FIG. 13 illustrates a second example of that illustrated in FIG. 11.

Referring now to FIG. 13, there is illustrated a flowchart for a second example for preparing a script for a cocktail, which is similar to the flowchart of FIG. 11. This is initiated at a block 1302 and then proceeds to a block 1304 to generate a script for a cocktail which is a patient-specific cocktail based upon a prick test performed. This is unique to that patient for that particular time. The program then proceeds to a function block 1306 in order to provide in that script a list of the antigens to be placed into the cocktail by the pharmacist, the final dilutant level of each, the dosage and the particular carrier. The program then flows to a function block 1308 in order to select the procedure that the pharmacist will utilize to provide this final diluted product with the prescribed number of dosages. This might be prescribed by the position or it might be selected by the pharmacist. The program then flows to a function block 1310 wherein the pharmacist performs the dilution operation and then combines various antigens into the cocktail, at a block 1312. The program then proceeds to a function block 1314 wherein the NDC for each antigen is entered into PM database, the dose level and the procedure. The program then proceeds to a function block 1316 to parse the particular antigens at the database, this parsing required in order to process each antigen in the database separately, as there must be a crosscorrelation back to each individual antigen, since only each individual antigen has an NDC associated there with. The program then proceeds to a function block 1318 in order to correlate the antigen back to the lowest concentrate NDC-carrying level, as described hereinabove with respect to the embodiment of FIGS. 11 and 12 and then to a function block 1320 in order to define the benefits and then to a function block 1322 in order to end the program, after the cocktail has been distributed to the end user such as the patient or the medical professional.

Figure 14:
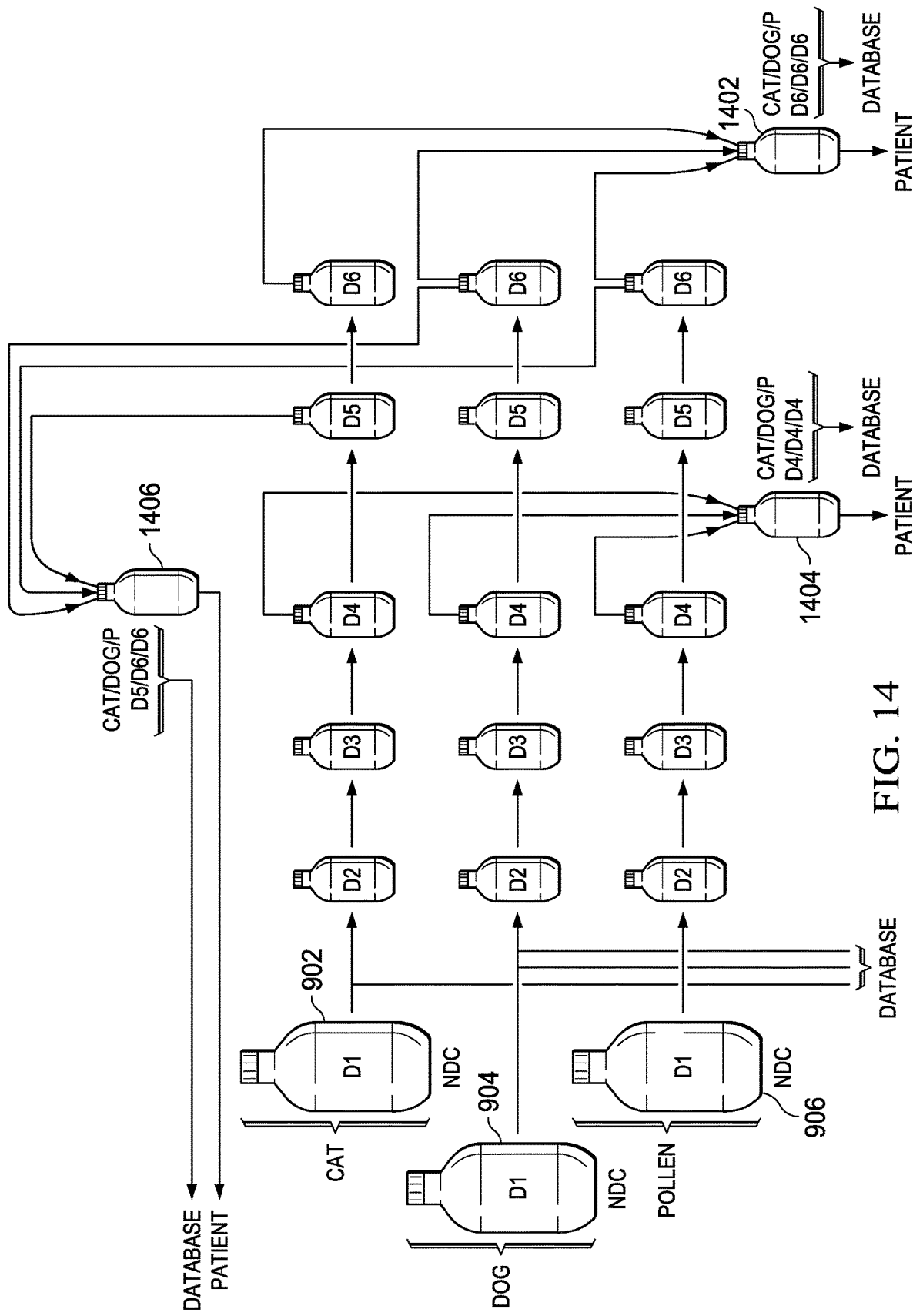
FIG. 14 illustrates a diagrammatic view of processing of a script received from a physician at a pharmacist to compound a patient-specific dosage.

Referring now to FIG. 14, there is illustrated a process, which is similar to that described hereinabove, for creating a cocktail from three different base concentrate antigens 902, 904 and 906, referring hereinabove to the description with respect to FIG. 9. These are diluted down in five separate steps to a final dilution level D6. In a first operation, there is provided a final vial 1402 that receives the final dosage from each of the processes for diluting the initial base concentrate levels. It may be that each of the final vials D6 each have 5 mL contained therein. By containing no carrier material in the final vial 1402, 3 mL of each of the extract can be placed therein resulting in a vial with 9 mL therein. If the physician prescribed the regimen to deliver a 1 mL dose of this concentrated level III times per week for three weeks, this would require nine doses and thus 9 mL of the cocktail. This overall process, for example, would require the pharmacist to understand each step of the dilution process to arrive at the final diluted. Thus, the pharmacist would indicate that there were three antigens in the final vial 1402 and that they were at the concentrate level D6/D6/D6. This would be provided to the PDM database. With this information alone, the system at the PDM database can cross correlate this back to the exact amount of base concentrate level lies for each of three base concentrate antigens 902, 904 and 906 utilized.

Alternatively, there is provided a vial 1404 which is the result of a different selection of cocktails from the D4 level. This, again, would have the re-antigens in the concentrate level D4/D4/D4. This would again pre-provided to the PDM database which would then, based upon the dilutant level for each of the antigens and the procedure utilized to achieve that dilutant level to relate this back to the antigens utilized at the NDC-carrying concentrate level. If, for example, this vial 1404 resulted in 9 mL of material but the physician only required three doses of 1 mL each for two weeks, this would only required 6.0 mL. The pharmacist might only dispense 6 mL out of the 9 mL to the patient or professional. Even though he doses distributed or 6.0 mL, this 6 mL of final product of D4/D4/D4 of Cat/Dog/Pollen antigen has to be related back to the original antigen value.

In an alternate embodiment, there is a vial 1406 provided that has been provided where in it receives diluted antigens from slightly different and vials. In this operation, the three antigens are D5/D6/D6 and this is provided back to the PDM database. Of interest is that all three vials 1402, 1404 and 1406 will each the input to the PDM system with their procedure and the result will be that, for this example specifically, at the reimbursable be the same, as the starting dilutant will be identical. This is procedure specific and script specific, with the cocktail noted as being patient-specific. The antigens/allergens 902, 904, and 906 may also have been part of the kit described with respect to FIG. 5. In that case, the pharmacist would still create a customized mix for the patient. For example, if the pharmacist received a kit for cat, dog, and pollen, and a prescription for a particular dosage of each (1 mL for example), the pharmacist would create a new bottle filled with one dose of antigen/allergen for cat, one dose for dog, and one dose for pollen. The dosage level (1 mL) may then be tracked back to the NDC code for each antigen/allergen. For example, if 1 mL of cat is associated with an NDC code having a price of $50 associated therewith, and the same is true for dog and pollen, then a total cost of $150 may be appropriate, allowing for the pharmacist to be reimbursed for that amount.

Figure 15:
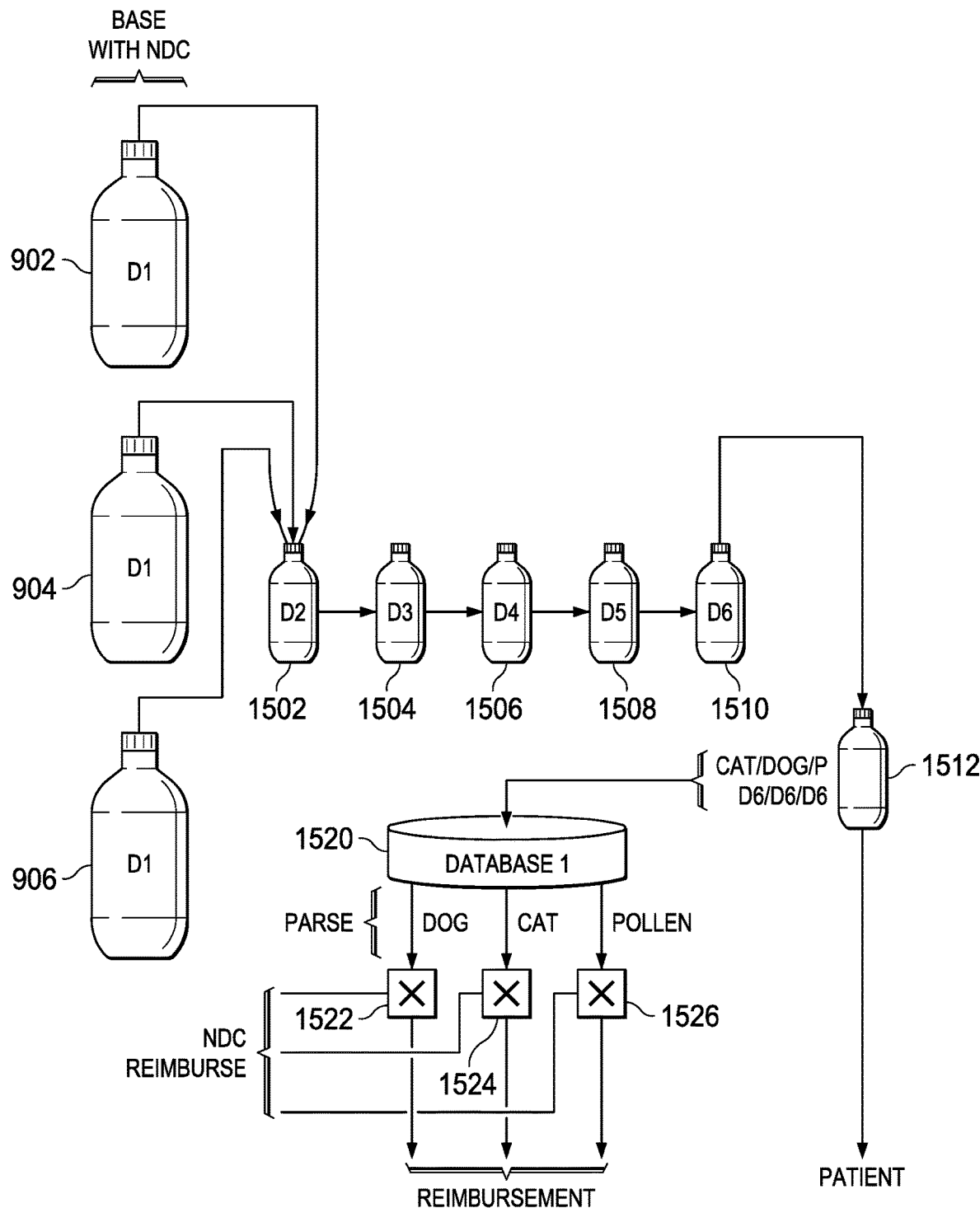
FIG. 15 illustrates an alternate embodiment of that illustrated in FIG. 14.

Referring now to FIG. 15, there is illustrated an alternate embodiment wherein each of the base antigens 902, 904 and 906 are subjected to a different procedure wherein each of the original starting amounts are input to a first diluting vial 1502 and are subsequently diluted through vials 1504, 1506, 1508 and 1510 to a final vial 1512. This is an distributed to the patient. This final vial represents the dilution at the vial 1510, which is D6/D6/D6. This, along with this is procedure is then transferred to the PDM database, as indicated by block 1520, which is then parsed to the specific antigens and into a translator associated with each antigen, indicated by a "X" for the crosscorrelation operation, blocks 1522, 1524 and 1526 associated with the Dog, Cat and Pollen antigens which will then define the reimbursement. Each translation block 1522 will be associated with a reimbursement database for defined benefits associated with the particular antigen. Of course, it is important to know the amount of antigen that was actually utilized in the overall procedure which, again, requires knowledge of the final script dilutant level of the antigen delivered to the patient and procedure for obtaining that diluted level.

Figures 16A, 16B:
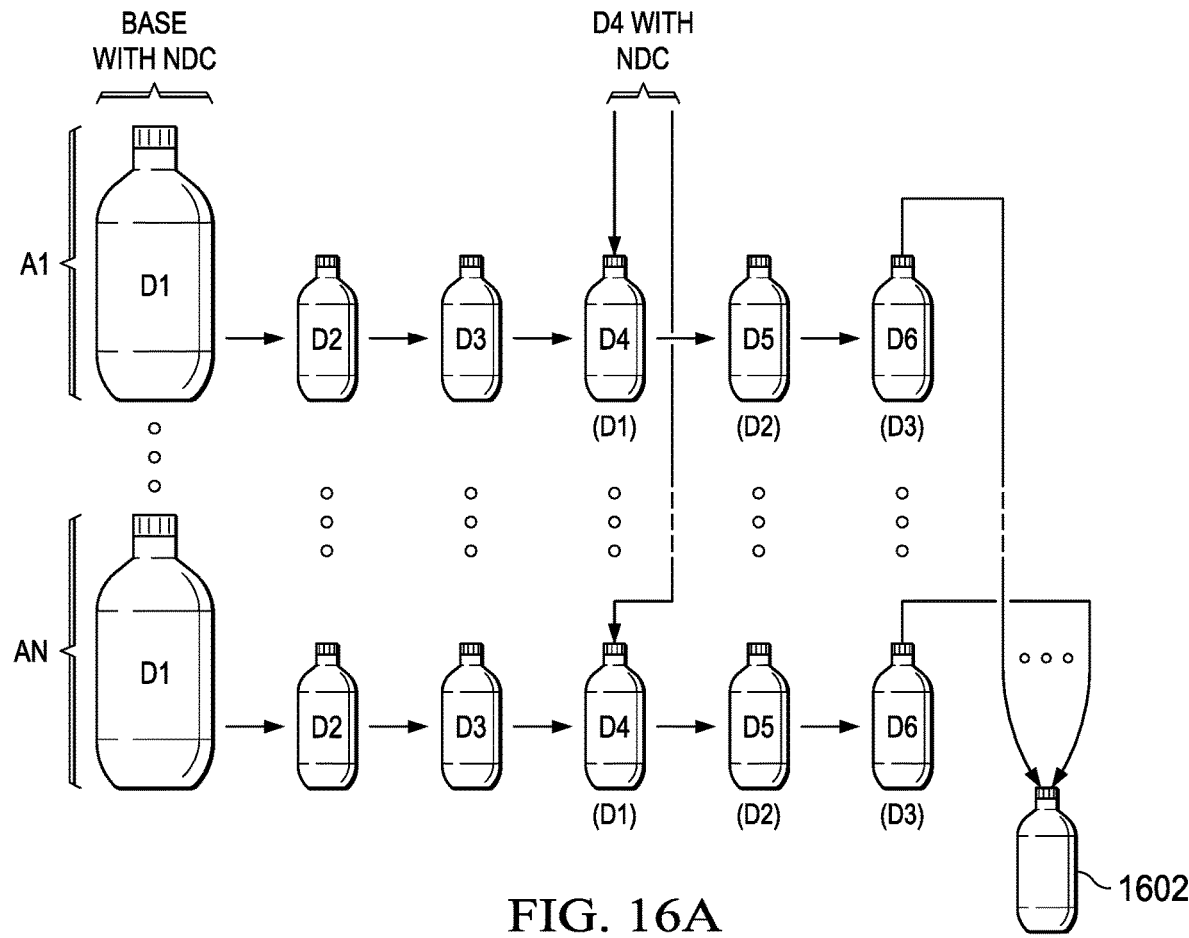
FIG. 16A illustrates a diagrammatic view of a process of filling a script received from a position and FIG. 16B illustrates a table associated with such process.

Referring now to FIG. 16A, there is illustrated a diagrammatic view of an overall process where in the NDC is associated with an intermediate level of dilutant. In this embodiment, the dilutant level D4 is illustrated as having an NDC associated there with, as well as the base concentrate level of Thus, it is possible that the reimbursement and be defined back to this intermediate concentrate level of. This is indicated in a table in FIG. 16B, wherein the table can have associated with original diluted levels D4, D5 and D6 crosscorrelation relationships with respect to the base concentrate level but, in this table, there are only three diluted levels required, the dilutant level for vial D4, the vial D5 and the vial D6. If the concentrate level at the final vial was X3 based upon the NDC code being at vial D4, all that would be required is to do a crosscorrelation back to the dilutant level required from the file D4. This would be for each of the dilutant set was combined in a vial 1602 from each of the antigens in the script, this indicated as being the antigens A1-N.

Figure 17:
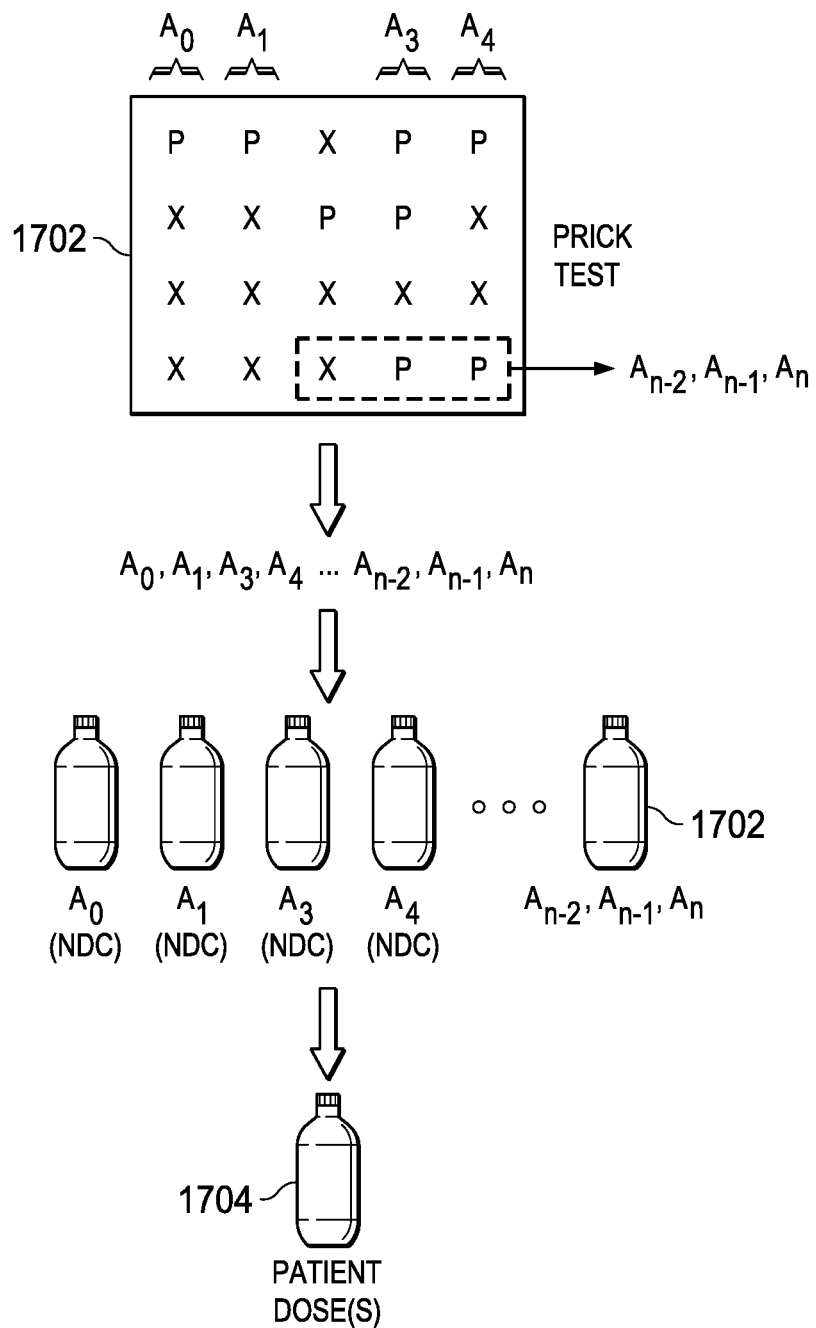
FIG. 17 illustrates an overall process flow illustrating the prick test, the script flowing through to the final patient does.

Referring now to FIG. 17, there is illustrated a process for mapping prick test to the script. As illustrated, there is provided a diagram of the prick test, indicated by a reference numeral 1702. This diagram 1702 indicates the locations of the particular allergens that were administered to locales on the person of the patient. This diagram illustrates the results with a "P" indicating a positive reaction and that an "X" indicating a negative reaction. Thus, the "P" indicates a sensitivity that must be considered in the script. Of interest is that the particular manufacturers of antigens might have a cocktail already existing in the base concentrate. This is illustrated with the bottom three test associated with antigens A(n−2), A(n−1) and AN. These are the last three antigens in the list. Of these, the last two are positive and the third for the last is negative. However, the script will have to include only the last two for the patient-specific script but the pharmacist only has the cocktail of all three available to them. Thus, the script will have a A0, A1, A3, A4 . . . , A(n−1) and AN as the antigens that are required for the desensitization regimen. This will be provided to the pharmacist which will then select NDC-Kerry antigen bottles A0, A1, A3, A4 . . . , And finally a bottle 1702 containing A(n−2), A(n−1) and AN, wherein only A(n−1) and AN are required in script to fill the prescription. This is then processed to provide the final patient dosage in the cocktail in the vial 1704.

Figures 18A, 18B:
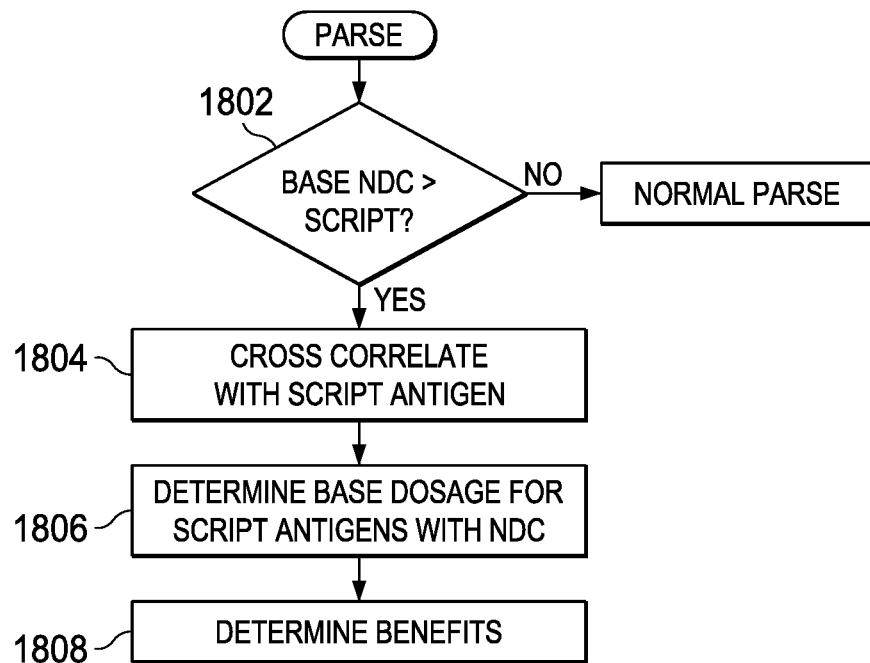
FIG. 18A illustrates a flowchart for parsing an antigen having a base dose with more than the prescribed antigens and FIG. 18B illustrates a table associated with the parsing operation.

Referring now to FIG. 18A, there is illustrated a flowchart depicting the overall parsing operation before the operation of FIG. 17. In this operation, if the base NDC has a greater number of antigens than the script, a decision block 1802 will determine such and flow to a block 1804. The program will then flow to a function block 1806 in order to determine the basis dosage for the script as required by and set forth by the position of the antigens with the particular NDC, even though that NDC IS associated with more than the antigens required by the script. The program then flows to a function block 1808 in order to determine the benefits. This is illustrated best with respect to the table of FIG. 18B. Here, it is illustrated that there are three procedures for providing the end dilutant level at the vial D6 for each of the antigens in the cocktail antigen vial 1702. If a certain amount of antigen is extracted from this particular vial 1702, it will contain all three antigens. At a particular concentrate level at the level D6, this will yield the necessary concentrated level of the two antigens desired even though the third antigen is included. Since the final dilutant level is known for the two prescribed antigens, they can be cross correlated back to the amount of antigen that was actually extracted. However, for example, if 3 mL of the extract in vial 1702 were extracted, this might represent a particular portion of a 100 mL bottle and, if all three antigens have been prescribed, this would be the basis for the reimbursement. However, if only to antigens were prescribed, only two thirds of that prescribed extract would be reimbursed. Thus, by utilizing known script at the known dilutant level, this can be cross correlated back via the standard procedure (or whatever procedure is utilized) to what was actually utilized of the NDC-carrying base concentrate material to actually derive the final prescribed and delivered antigen to the patient.

Figure 19:
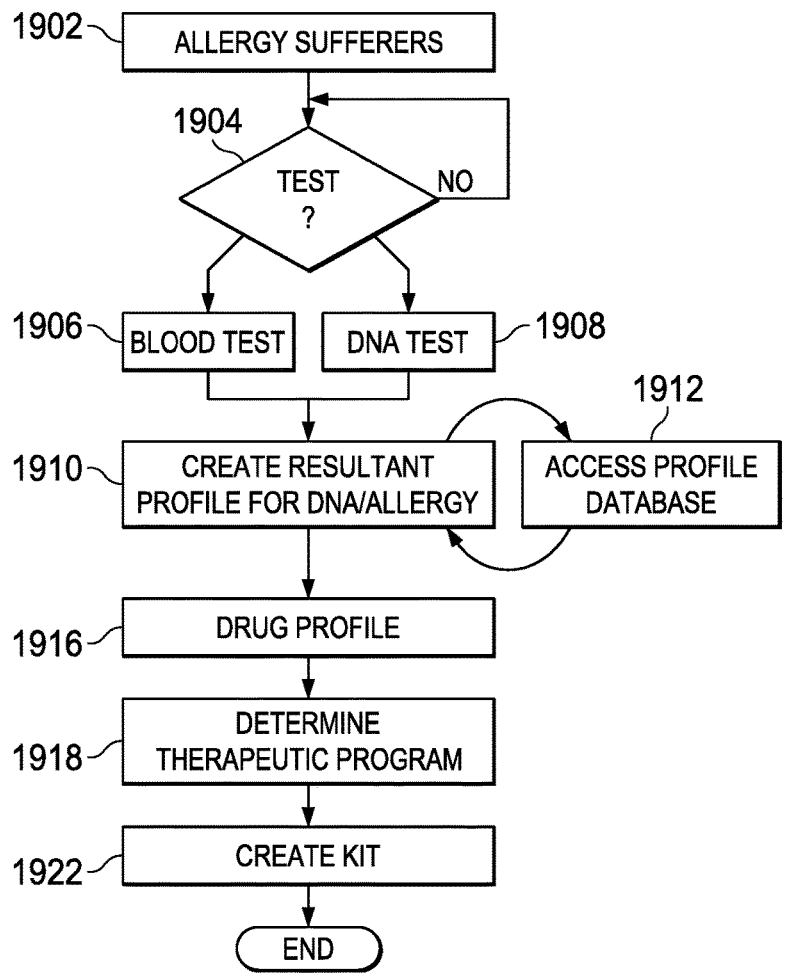
FIG. 19 illustrates a flow chart for the general operation of creating a kit based upon a resultant DNA profile.

Referring now to FIG. 19, in an alternate embodiment, there is illustrated a flowchart depicting the creation of kit for an allergy sufferer based on blood and/or DNA tests. This is initiated at a block 1902 and proceeds to a decision block 1904 to determine if a profile testing has been performed. This particular test utilizes a blood test and/or a DNA test in combination. These are represented by blocks 1906 and 1908, respectively. The blood test in block 1906 can be utilized to determine the allergy susceptibility of a patient, noting that this allergy test could be performed by the conventional "prick" test. The DNA test could be a blood test or a "swab" test. With the DNA test, the genetic information assessed by an individual in the form of the human genome associated therewith can be determined. By being able to look at genes associated with the health of an individual, it is possible to assess responses too. The information that can be learned from the past serves to help diagnose disease, identify gene changes that are responsible for an already diagnosed disease, determine the severity of a particular disease, assist physicians in deciding the best medicine or treatment to use for certain individuals, identify gene changes that increase the risk to develop a disease, identify gene changes that could be passed on to children, screen newborn babies for certain treatable conditions, etc. Genetic test results can be hard to understand, however. Specialists like geneticists and genetic counselors can provide information with respect to these tests and associate a therapeutic program therewith. These therapeutic programs can be defined in a database in association with the genetic profile defined by the DNA test. However, when using the association with a particular allergy test, a particular resultant profile will be created as defined in a block 1910 for both a DNA and an allergy test. A profile database is provided and accessed to create this profile, as defined in a block 1912. This is a predetermined default database that associates the various drug-allergy reactions together and different therapeutic programs. With this resultant profile, it is possible to determine a therapeutic program for an individual. This therapeutic program is based on the profile of a particular individual with respect to their specific DNA profile and their specific determined allergic susceptibilities. Thus, the use of both a DNA test and an allergy test in association with a knowledge database about the interactions of various drug-supplement-allergen reactions enables generation of this profile. For example, if the patient is known to be taking the drug Lipitor, there are known interactions with various allergens. These allergens are weighted by individuals taking Lipitor. The profile of an individual, of course, also involves knowledge of drugs being taken. Thus, when combining the allergy test and the DNA test to provide a resultant profile and then utilizing a drug profile for such things as prescribed drugs, as indicated in a block 1916, a therapeutic program can be determined, as in a block 1918. It may be that a particular DNA profile associated with a particular allergen requirement would also result in a determination that a particular antihistamine drug or the such would be required in combination therewith and that the genetic makeup of an individual allows such. It can also be determined that a particular allergen might require the addition of a particular vitamin or supplement in association therewith. For example, is known that certain supplements, when taken by themselves, have less of an effect than when taken in association with other supplements. There's also the case that certain drugs are known to have more effectiveness or less effectiveness when taken in association with other drugs and/or supplements. Thus, based upon the DNA profile of a particular individual, complementary products can be added to a treatment regimen for a particular allergen. This is based on various determined deficiencies from the DNA profile that, when combined with a particular allergen, results in a predetermined need for a particular supplement or the such.

Once a therapeutic program is determined, allergens are combined with the various supplements and drugs in a kit, as indicated by block 1922.

Figure 20:
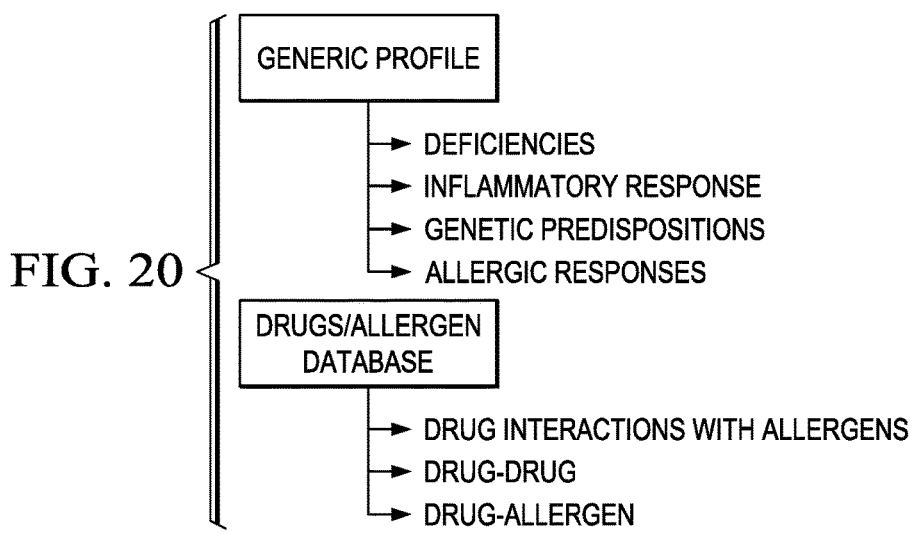
FIG. 20 illustrates a diagrammatic view of the generation of a genetic profile in Association with a drug/allergen database showing the drug-allergen reactions.

Referring now to FIG. 20, there is illustrated a diagrammatic view of the genetic profile and the drugs-allergen database. The genetic profile generally will provide information to a geneticist and to a database information regarding such things as certain deficiencies, certain inflammatory responses, certain genetic predispositions and certain allergic responses. This is primarily based on genetic information related to genetic makeup of a particular genome of an individual. There's also provided a drug-allergen database which provide such things as drug interactions with particular allergens, drug-drug interactions, and drug-allergen interactions. This information is utilized to create the particular profile that is then associated with a particular program.

Figure 21:
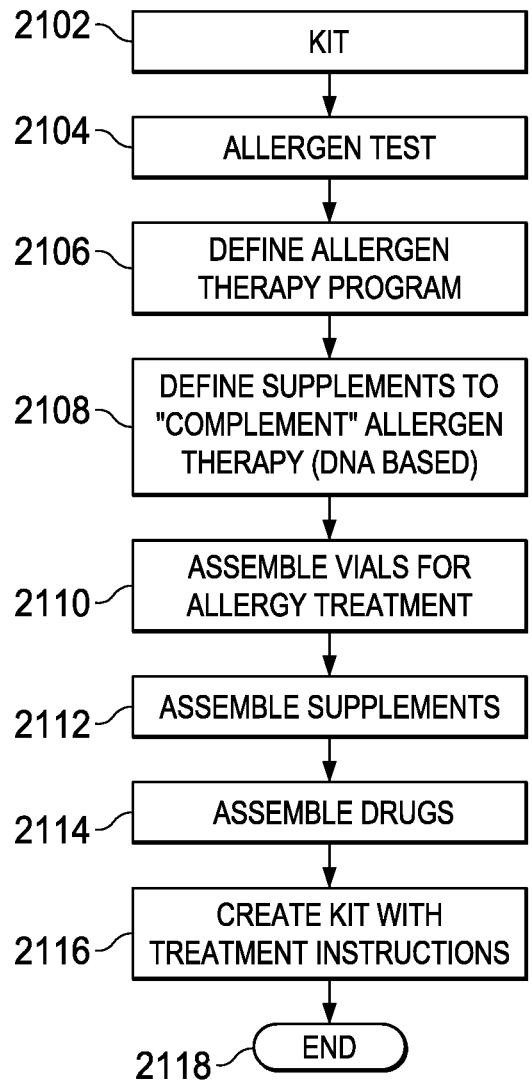
FIG. 21 illustrates a flow chart for generating a kit.

Referring now to FIG. 21, there is illustrated a flowchart for creating a particular kit for an individual, this kit being a kit that can be utilized by the individual to treat their allergy, as determined by the allergy tests, and also provide such to provide an overall therapeutic regimen. This is more than just receiving an allergy shot on a regular basis but, rather, also provides products to complement the allergy regimen based upon the DNA profile. As noted above, it may be that some supplements such as a vitamin would effectively improve the overall regimen. Additionally, it may be that, for example, a determination of an allergy to hayfever could require a particular antihistamine for that individual. With the DNA profile, it is possible to gain knowledge that an antihistamine of a particular type is better for that individual or it may be that the individual would be prohibited from having any antihistamine as part of their therapeutic regimen. The DNA profile can provide this information.

The flowchart is initiated at a block 2102 and then proceeds to block 2104 to perform the allergy test, which, as noted hereinabove can be a blood test or a prick test. The program then proceeds to a block 2106 to define an allergen therapy program, which, in part, provides for a sequence of injections of allergens. This sequence of allergens and the technique for creating the various dilutions is illustrated in FIG. 1.

In a kit, what is important is that a regimen be provided wherein the latest dose is prescribed for possibly two weeks at a rate of three times per week, a second dose is prescribed for the third week at a dose of three times per week, a fourth week is associated with a third dose and a fifth week is associated with a fourth dose. Each of the doses is increasing in the amount of allergen, such that the most diluted dose is utilized initially and the more concentrated dose is utilized at a later time.

Referring back to FIG. 21, when the allergen regimen has been defined, various supplements that will complement the allergen therapy are defined, these being DNA-based, as indicated by block 2108. The vials for the allergy treatment are then assembled, being at the prescribed dosage increments, each vial being approximately 5 mL in size for possibly multiple doses, a typical dose being 1 mL. This is indicated at a block 310. The supplements are then assembled with the vials, as indicated by a block 2112 and then any drugs that may be associated with the therapeutic treatment are assembled, as indicated by block 2114. The kit is then created with treatment instructions associated therewith, as indicated by block 2116. The flowchart then proceeds to an END block 2118.

Figure 22:
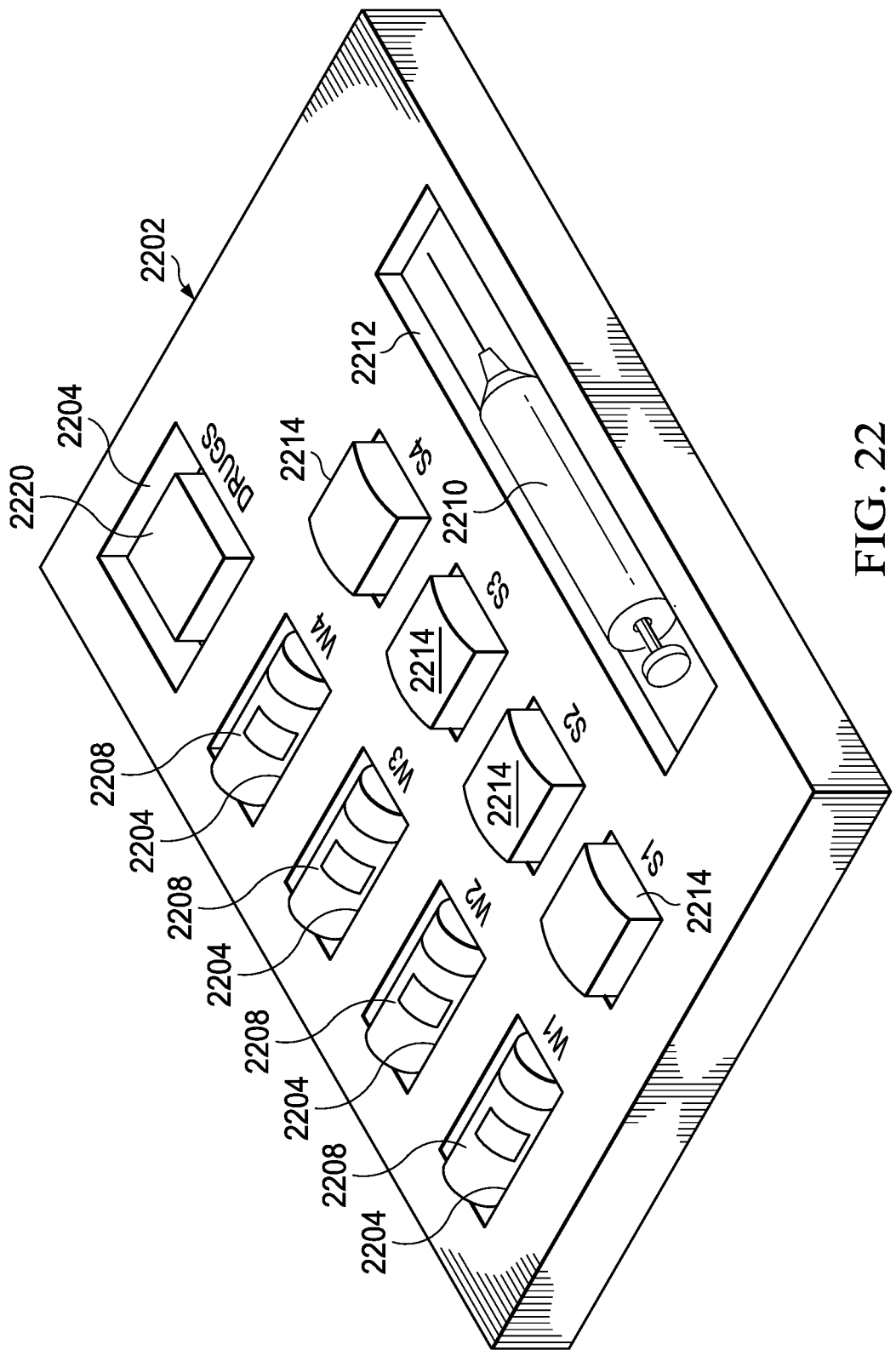
FIG. 22 illustrates a therapeutic treatment kit.

Referring now to FIG. 22, there is illustrated and assembled kit 2202. The kit 2202 is comprised of a plurality of compartments for containing various constituents of the kit. The kit can comprise separate vials of antigens 2208, each disposed in a separate compartment and marked by the particular week it is associated therewith. In this particular example, there is one vial 2208 associated with each week. The regimen would be to extract from a particular vial 2208 a single dose for multiple times per week. The size of the vial 2208 is 5 mL, a standard in the industry, but a particular dose of antigen would be approximately 1 mL. Thus, if the regimen prescribed three doses in a given week, the individual would select the vial 2208 associated with WI and extract the dose therefrom. There is provided at least one hypodermic needle 2210 in a compartment 2212. There can be multiple hypodermic needles, but one is all that is necessary. Of course, each time the hypodermic needle 2210 is used, a sterile cap on the vial 2208 will be broken. Thus, there may be multiple hypodermic needles 2210 provided in the kit. In addition to the separate vials 2208 of antigen, there is also provided a plurality of different supplements 2214, each of the supplements being different and associated with a particular regimen. There also may be provided one or more drugs 2220 in one of the compartment 2204 labeled DRUGS.

Thus, for a regimen, there will be provided in the kit 2202 associated instructions for a particular and unique therapeutic program, it being noted that this particular kit 2202 is designed for a therapeutic regimen that is based upon a determination of the allergy susceptibilities of a particular individual and their DNA profile. This therapeutic program, in the instant case illustrated in FIG. 22, will possibly require the individual to administer shots of different doses of allergens associated with different weeks. In addition, during that time, various supplements would be taken at a particular time. In addition, drugs are provided which may be drugs that are prescribed in accordance with the regimen or, alternatively, may be drugs that are prescribed for the individual separately. For example, the individual may already be on Lipitor. This particular regimen could be designed for an individual with a particular DNA profile, a particular allergy susceptibility and knowledge that the individual was using Lipitor. This drug could be provided in the kit 2202. However, this drug 2220 could also be an OTC drug such as an antihistamine.

Figure 23:
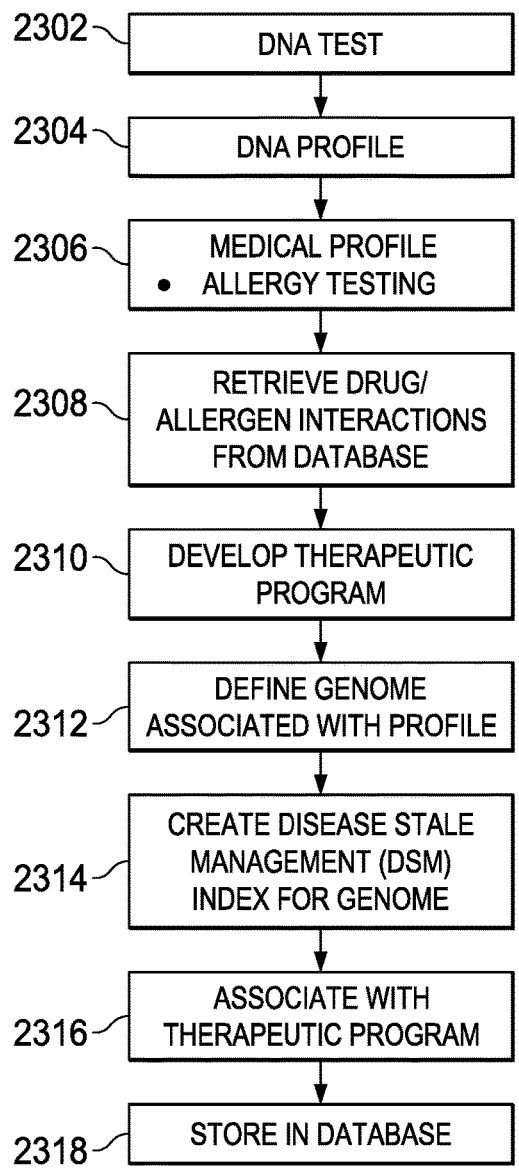
FIG. 23 illustrates a flowchart for creating a Disease State Management (DSM) index for a genome associated with that management program.

When considering the kit 2302 of FIG. 23, is important to note that this is a unique configuration of a patient specific regimen based upon the patient's profile that is correlated with interactions between drugs, antigens and supplements. For example, the vials of antigen 2308 would not provide, in and of themselves, a particular desensitization regimen at the level desired by a practitioner if they were prescribed apart from any of the supplements or drugs that are disposed in the kit. The reason for this is that the practitioner, when operating within a vacuum and only information from, for example, a prick test, would design the antigen delivery regimen differently if not for correlation with other factors. By correlating the desensitization regimen with other factors, such as those derived from patient profile, their history, a DNA test, etc., and correlating this with no drug interactions, a physician can now architect and prescribe the unique kit that will take into account the various facts when the particular physician has knowledge that the patient is taking a particular drug. So, if, for example, the drug were an antihistamine or Plavix, in one example, the physician could look at drug interactions to correlate this with the desired diluted levels necessary for a desensitization program and also combine this with known supplements that can affect your overall therapeutic regimen. Comparing this, for example, to a physician that looks primarily at drug interactions for a patient taking multiple drugs and the such, this physician would suggest that a particular prescription for the antigens, for example, be adjusted in one direction from a standalone desensitization regimen, the local antihistamine be adjusted from a standalone prescription in another direction and particular supplements possibly be prescribed in accordance with the need. It may be that the individual already takes a particular supplement regimen for dietary purposes or the such and wants to maintain that particular supplement regimen. The supplements could be maintained at one level and, based upon the DNA profile and the various correlations with the drug interactions retrieved from a known database, antigen regimen antidrug regimen could be altered to maintain the supplement regimen or, alternatively, the supplement regimen could be modified. However, the number and type of supplements could be maintained. Also, by combining all of individual correlated and defined drugs, diluted antigens and supplements into a single kit that is packaged with instructions for a particular individual based upon all of the information determined from the patient's profile, their DNA profile, the drug interaction databases and relationships therebetween, this kit has the ability to be associated with a prescription and to provide a sterilized package for a particular patient for that particular regimen. Thus, the instructions may instruct the individual how to administer all of this during the first week, in one example, wherein antigen from the vial 2308 labeled W1 is selected for the first week. This diluted antigen may be contained in a 5 mL bottle having five doses which might be distributed (in accordance with the instruction) over five days or, alternatively, there could be five 1 mL bottles contained in five inserts. These would be single-dose bottles, as described hereinabove. Each of the supplement containers 2314 could contain multiple pills or capsules. The directions would instruct that a particular supplement be taken one day immediately with an injection or shortly thereafter. Instructions could also indicate that the drugs in the bottle 2320 in the insert 2304 associated there with be taken possibly once per day in the morning. The kit is a unique and complete kit unique to that patient and the prescribed regimen, in that the entire regimen could be designed for four weeks to get to the most diluted antigen in bottle 2308 associated with W4, associated with the fourth week. There would be enough supplements in the kit, enough doses of antigens and enough pills to provide a single cohesive regimen for that patient which is uniquely cross correlated with their DNA profile, their history and with drug interactions between the multiple items contained within the kit. This is distinctly different than a physician merely determining drug interactions and adjusting each drug individually. This provides an entire cohesive single regimen that is all integrated for a single patient, disposed in a kit with instructions and then packaged for that individual in a sterile environment. Even though the packaging is not illustrated, it would be a sealed package sealed at the compound pharmacist, for example, with instructions, which is provided in accordance with conventional means. Again, the antigen could be in a multi-dose vials or in single-dose vials.

Referring now to FIG. 23, there is illustrated a flowchart for creating a Disease State Management (DSM) index for a genome associated with that management program. The program was initiated at a block 2302 to perform a DNA test and then to create the DNA profile at a block 2304. Once the DNA profile is determined for a particular individual, a medical profile for that individual can be determined which is then associated with another step of allergy testing, as described hereinabove. This is indicated at a block 2306. At a block 2308, a database is accessed to determine the drug-allergen interactions that could possibly exist with respect to a particular medical profile associated with an individual. Once the DNA profile is understood and, in response to a determination of allergy susceptibilities of the particular individual and a potential need for a particular allergen for that individual, any drug interactions with respect to that allergen can be determined from this external database.

A therapeutic program is developed for a particular medical profile associated with the DNA profile primarily and the genome. A particular individual's genome makeup will define a particular therapeutic regimen. For a particular genome not necessarily considering the allergy susceptibilities associated with that particular genome makeup, a therapeutic program can be developed, as indicated in a block 2310. The therapeutic program can treat multiple different maladies and can be directed toward allergy susceptibilities, without an actual allergy test. The DNA profile itself shows the susceptibilities. Geneticists and the such can develop this program to medically treat allergies. Once the particular genome makeup is defined, that genome makeup is relatively unique and associated with a unique medical treatment or therapeutic program by a geneticists or some other professional. This is facilitated by such things as drug-drug interactions, drug-allergen interactions, etc. The geneticist, by reviewing the particular genome makeup, can determine certain supplement needs, allergen needs, etc. for a particular individual with that genome makeup. Once the particular therapeutic program is developed and associated with that particular profile or genome makeup, a genome is defined as associated with that particular therapeutic program or profile, as indicated by block 2312. Thereafter, indexes are created for that particular association which is defined as the Disease State Management (DSM) index. This index provides the ability to define in a database a particular genome or DNA profile in association with a predetermined therapeutic program which was determined based upon that particular DNA profile. By analyzing a large number of layouts for a particular genome makeup, that particular genome makeup can be associated with a particular therapeutic program and an index. Thereafter, all that is necessary is to determine the genome-DSM relationship and the therapeutic program can be accessed thereafter.

In general, a particular genome makeup for an individual may not entirely match any of the genomes in the database. Thus, there may have to be some type of heuristic algorithm utilized to select the best match to that genome and then the index accessed to access the therapeutic program. Once the DSM index is accessed, and the therapeutic program is accessed, this DSM index can also be associated with a particular kit makeup, such that, utilizing the DSM index, the kit can be created. Thus, the DSM index is created in a database, as indicated by a block 2314, and associated with the therapeutic program, as indicated by block 2316, and is stored in the defined database, as indicated by block 2318.

Figure 24:
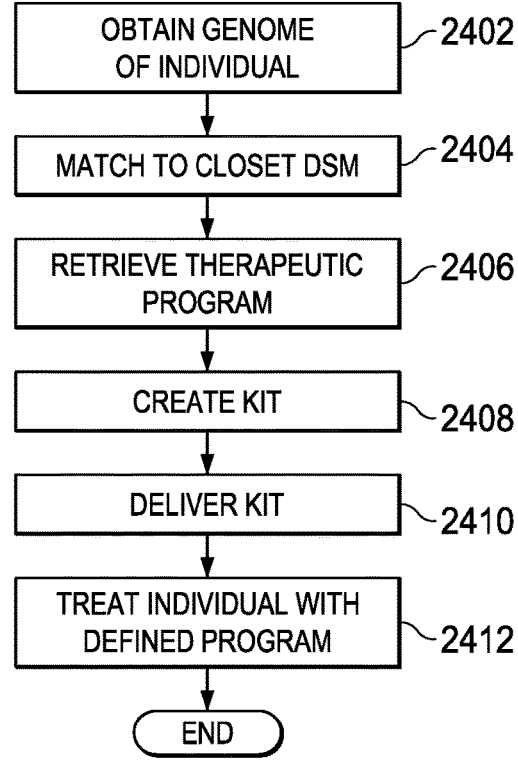
FIG. 24 illustrates a flowchart depicting actual kit creation and treatment.

Referring now to FIG. 24, there is illustrated a flowchart depicting the actual kit creation and treatment. The program is initiated at a block 2402 to obtain the genome of an individual and then to a block 2404 to match the genome of that individual, i.e., their genome makeup, to the closest DSM. As noted hereinabove, some type of heuristic algorithm can be utilized for such an operation. The program then flows to a block 2406 to retrieve the basic therapeutic program associated with that DSM and also the kit that will be associated with that DSM, as indicated by block 2408. This kit is created and then delivered, as indicated by block 2410. Once delivered, the individual is treated with the defined therapeutic program that is associated with that particular kit and instructions associated therewith, as is indicated by a block 2412.

Although the preferred embodiment has been described in detail, it should be understood that various changes, substitutions and alterations can be made therein without departing from the spirit and scope of the invention as defined by the appended claims.

What is claimed is:

1. A therapeutic treatment kit unique to an individual patient, comprising:
   a container holding a plurality of compartmentalized therapeutic dispensers;
   the therapeutic dispensers including:
      a plurality of vials of antigens, at least select ones of each of the vials of antigens having a dilution level with respect to a base extract and each disposed in a compartment with a notation as to the dilution level and a dispensing period and wherein the dilution level of each of the select ones of each of the vials is defined for the individual patient based upon predetermined sensitivities;

a plurality of containers of supplements disposed in compartments of the therapeutic treatment kit, each of the compartments labeled with a name of the supplement;

at least one container of drugs, wherein a quantity of the drugs can be dispensed from the at least one container of drugs;

a compartment for containing applicators for the antigens, such that an individual can extract the antigen from the vial in a single dose; and instructions associated with a unique therapeutic program for utilizing the vials of antigens, the supplements and the drugs in accordance with a therapeutic program that is predefined, wherein a construction of the kit, including dosages of the antigen, types of antigens, the dilution level of each of the select ones of each of the vials, and a number and types of supplements are all associated with the unique therapeutic program, wherein the unique therapeutic program is unique to the individual patient based on a matching of a genome of the individual patient to a disease state management (DSM) index, and wherein, for the individual patient, there exists a determined correlation between a desensitization therapeutic regimen for the dilution and amount of antigens to be administered over a finite period of time, the amount and frequency of supplements to be taken in association with the administration of the antigens over the finite period of time and the amount and frequency of the quantity of the drugs to be taken in association with the administration of the antigens over the finite period of time and a database of known information and patient specific information, and the amount of antigens, supplements and drugs are limited in the kit to the finite period of time as to quantity so as to be completely used up in the administration of the unique therapeutic program.

2. The therapeutic treatment kit of claim 1, wherein each of the vials of antigens contained a single dose of the associated diluted antigen.

3. The therapeutic treatment kit of claim 1, wherein the drugs in the at least one container of drugs includes a pill.

4. The therapeutic treatment kit of claim 1, wherein the correlation with a database of known information comprises correlation with a database of drug interaction information defined interaction between the drugs contained in the at least one container of drugs and the antigens and the supplements.

5. The therapeutic treatment kit of claim 4, wherein the patient specific information is based on a patient profile for the individual patient defining a medical history of the individual patient.

6. The therapeutic treatment kit of claim 1, wherein each of the compartments for each of the plurality of compartmentalized therapeutic dispensers are labeled.

7. The therapeutic treatment kit of claim 1, wherein the therapeutic treatment kit is contained within sterilized packaging.

8. The therapeutic treatment kit of claim 1, wherein the therapeutic treatment kit is prescribed by a physician.

* * * * *